United States Patent
Merriman et al.

(10) Patent No.: US 12,247,251 B2
(45) Date of Patent: *Mar. 11, 2025

(54) ENZYMATIC CIRCUITS FOR MOLECULAR SENSORS

(71) Applicant: Roswell Biotechnologies, Inc., San Diego, CA (US)

(72) Inventors: Barry L. Merriman, La Jolla, CA (US); Venkatesh Alagarswamy Govindaraj, San Diego, CA (US); Paul Mola, San Diego, CA (US); Tim Geiser, San Diego, CA (US)

(73) Assignee: Semicon Bio, San Diego, CA (US)

( * ) Notice: Subject to any disclaimer, the term of this patent is extended or adjusted under 35 U.S.C. 154(b) by 718 days.

This patent is subject to a terminal disclaimer.

(21) Appl. No.: 17/138,314

(22) Filed: Dec. 30, 2020

(65) Prior Publication Data

US 2022/0002777 A1    Jan. 6, 2022

Related U.S. Application Data

(60) Continuation of application No. 16/878,484, filed on May 19, 2020, now Pat. No. 10,913,966, which is a division of application No. 16/684,338, filed on Nov. 14, 2019, now Pat. No. 11,268,123, which is a continuation of application No. 16/015,028, filed on Jun. 21, 2018, now Pat. No. 10,508,296, which is a continuation of application No. PCT/US2018/029382, filed on Apr. 25, 2018.

(60) Provisional application No. 62/489,881, filed on Apr. 25, 2017.

(51) Int. Cl.
| | |
|---|---|
| *C12Q 1/6869* | (2018.01) |
| *C07H 21/02* | (2006.01) |
| *C12Q 1/00* | (2006.01) |
| *C12Q 1/26* | (2006.01) |
| *C12Q 1/48* | (2006.01) |
| *C12Q 1/6825* | (2018.01) |
| *G01N 33/543* | (2006.01) |

(52) U.S. Cl.
CPC .......... *C12Q 1/6869* (2013.01); *C07H 21/02* (2013.01); *C12Q 1/001* (2013.01); *C12Q 1/002* (2013.01); *C12Q 1/005* (2013.01); *C12Q 1/26* (2013.01); *C12Q 1/48* (2013.01); *C12Q 1/485* (2013.01); *C12Q 1/6825* (2013.01); *G01N 33/5438* (2013.01); *G01N 2333/9126* (2013.01)

(58) Field of Classification Search
None
See application file for complete search history.

(56) References Cited

U.S. PATENT DOCUMENTS

| | | |
|---|---|---|
| 4,923,586 A | 5/1990 | Katayama et al. |
| 5,082,627 A | 1/1992 | Stanbro |
| 5,194,133 A | 3/1993 | Clark et al. |
| 5,366,140 A | 11/1994 | Koskenmaki et al. |
| 5,414,588 A | 5/1995 | Barbee, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,646,420 A | 7/1997 | Yamashita |
| 5,767,687 A | 6/1998 | Geist |
| 5,871,918 A | 2/1999 | Thorp et al. |
| 5,881,184 A | 3/1999 | Guidash |
| 5,965,452 A | 10/1999 | Kovacs |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |

(Continued)

FOREIGN PATENT DOCUMENTS

| | | |
|---|---|---|
| CN | 1795376 | 6/2006 |
| CN | 101231287 | 7/2008 |

(Continued)

OTHER PUBLICATIONS

USPTO; Requirement for Restriction dated Nov. 2, 2011 in U.S. Appl. No. 12/667,583.

(Continued)

*Primary Examiner* — Amanda Haney
(74) *Attorney, Agent, or Firm* — Spectrum IP Law Group (SLGIP); Dianoosh Salehi

(57) ABSTRACT

In various embodiments a molecular circuit is disclosed. The circuit comprises a negative electrode, a positive electrode spaced apart from the negative electrode, and an enzyme molecule conductively attached to both the positive and negative electrodes to form a circuit having a conduction pathway through the enzyme. In various examples, the enzyme is a polymerase. The circuit may further comprise molecular arms used to wire the enzyme to the electrodes. In various embodiments, the circuit functions as a sensor, wherein electrical signals, such as changes to voltage, current, impedance, conductance, or resistance in the circuit, are measured as substrates interact with the enzyme.

15 Claims, 16 Drawing Sheets

(56) References Cited

U.S. PATENT DOCUMENTS

| | | |
|---|---|---|
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 10,913,966 B2 | 2/2021 | Merriman et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 | 7/2003 | Lee et al. |
| 2003/0141276 A1 | 7/2003 | Lee et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1 | 8/2007 | Curry et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1 | 1/2008 | Li et al. |
| 2008/0098815 A1 | 5/2008 | Merassi et al. |
| 2008/0149479 A1 | 6/2008 | Olofsson et al. |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0035254 A1 | 2/2010 | Williams et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1* | 7/2010 | Steinmuller-Nethl ........ G01N 33/5438 435/6.19 |
| 2010/0188109 A1 | 7/2010 | Edel et al. |
| 2010/0194409 A1 | 8/2010 | Gao et al. |
| 2010/0201381 A1 | 8/2010 | Iqbal et al. |

(56) References Cited

U.S. PATENT DOCUMENTS

| | | |
|---|---|---|
| 2010/0206367 A1 | 8/2010 | Jeong et al. |
| 2010/0227416 A1 | 9/2010 | Koh et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci |
| 2011/0065588 A1 | 3/2011 | Su et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1 | 5/2012 | Gao et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1 | 12/2012 | Eichen et al. |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0048776 A1 | 2/2014 | Huang et al. |
| 2014/0054788 A1 | 2/2014 | Majima et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0027775 A1 | 6/2014 | Quick et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1 | 10/2014 | Chou et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1* | 1/2015 | Huang .......... C12Q 1/6874 |
| | | 435/6.19 |
| 2015/0049332 A1 | 2/2015 | Sun et al. |
| 2015/0057182 A1 | 2/2015 | Merriman et al. |
| 2015/0065353 A1 | 3/2015 | Turner et al. |
| 2015/0068892 A1 | 3/2015 | Ueno et al. |
| 2015/0077183 A1 | 3/2015 | Ciubotaru |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0290957 A1 | 10/2016 | Ram |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1* | 2/2017 | Turner ............. H01L 29/1606 |
| 2017/0038333 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1 | 10/2017 | Majima et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |
| 2020/0242482 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |
| 2021/0048405 A1 | 2/2021 | Merriman et al. |
| 2021/0077998 A1 | 3/2021 | Choi et al. |

FOREIGN PATENT DOCUMENTS

| | | |
|---|---|---|
| CN | 102706940 | 10/2012 |
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | H0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |

(56) References Cited

FOREIGN PATENT DOCUMENTS

| WO | 2009035647 | 3/2009 |
|---|---|---|
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2003091458 | 1/2019 |

OTHER PUBLICATIONS

USPTO; Non-Final Office Action dated Sep. 28, 2018 in U.S. Appl. No. 12/667,583.
USPTO; Final Office Action dated Feb. 19, 2019 in U.S. Appl. No. 12/667,583.
USPTO; Non-Final Office Action dated Aug. 19, 2019 in U.S. Appl. No. 12/667,583.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Advisory Action dated Mar. 14, 2017 in U.S. Appl. No. 15/050,270.
USPTO; Final Office Action date Dec. 30, 2016 in U.S. Appl. No. 15/050,270.
USPTO; Non-Final Office Action dated Sep. 29, 2017 in U.S. Appl. No. 15/050,270.
USPTO; Final Office Action dated Jul. 10, 2018 in U.S. Appl. No. 15/050,270.
USPTO; Advisory Action dated Sep. 26, 2018 in U.S. Appl. No. 15/050,270.
USPTO; Non-Final Office Action dated Feb. 26, 2019 in U.S. Appl. No. 15/050,270.
USPTO; Final Office Action dated Jul. 10, 2019 in U.S. Appl. No. 15/050,270.
USPTO; Notice of Allowance dated Jan. 6, 2020 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Jan. 17, 2017 in U.S. Appl. No. 15/336,557.
USPTO; Non-Final Office Action dated May 16, 2017 in U.S. Appl. No. 15/336,557.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Non-Final Office Action dated Feb. 9, 2018 in U.S. Appl. No. 15/728,400.
USPTO; Final Office Action dated Jul. 10, 2018 in U.S. Appl. No. 15/728,400.
USPTO; Advisory Action dated Oct. 12, 2018 in U.S. Appl. No. 15/728,400.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Non-Final Office Action dated Feb. 23, 2018 in U.S. Appl. No. 15/728,412.
USPTO; Final Office Action dated Jun. 13, 2018 in U.S. Appl. No. 15/728,412.
USPTO; Notice of Allowance dated Sep. 12, 2018 in U.S. Appl. No. 15/728,412.
USPTO; Non-Final Office Action dated Feb. 23, 2018 in U.S. Appl. No. 15/796,080.
USPTO; Final Office Action dated Jun. 14, 2018 in U.S. Appl. No. 15/796,080.
USPTO; Advisory Action dated Sep. 4, 2018 in U.S. Appl. No. 15/796,080.
USPTO; Notice of Allowance dated Oct. 11, 2018 in U.S. Appl. No. 15/796,080.
USPTO; Non-Final Office Action dated Mar. 7, 2019 in U.S. Appl. No. 15/944,356.
USPTO; Non-Final Office Action dated Sep. 4, 2018 in U.S. Appl. No. 15/979,135.
USPTO; Advisory Action dated May 22, 2019 in U.S. Appl. No. 15/979,135.
USPTO; Non-Final Office Action dated Jun. 25, 2019 in U.S. Appl. No. 15/979,135.
USPTO; Final Office Action dated Mar. 1, 2019 in U.S. Appl. No. 15/979,135.
USPTO; Non-Final Office Action dated Nov. 30, 2018 in U.S. Appl. No. 15/979,135.
USPTO; Notice of Allowance dated Dec. 11, 2019 in U.S. Appl. No. 15/979,135.
USPTO; Non-Final Office Action dated Aug. 22, 2019 in the U.S. Appl. No. 16/011,065.
USPTO; Final Office Action dated Mar. 6, 2020 in U.S. Appl. No. 16/011,065.
USPTO; Requirement for Restriction dated Oct. 15, 2018 in U.S. Appl. No. 16/015,028.
USPTO; Non-Final Office Action dated Dec. 26, 2018 in U.S. Appl. No. 16/015,028.
USPTO; Final Office Action dated Apr. 15, 2019 in U.S. Appl. No. 16/015,028.
USPTO; Non-Final Office Action dated Jul. 30, 2019 in the U.S. Appl. No. 16/015,028.
USPTO; Notice of Allowance dated Nov. 8, 2019 in U.S. Appl. No. 16/015,028.
USPTO; Requirement for Restriction dated Dec. 17, 2018 in U.S. Appl. No. 16/015,049.
USPTO; Non-Final Office Action dated Mar. 6, 2019 in U.S. Appl. No. 16/015,049.
USPTO; Final Office Action dated Jun. 19, 2019 in U.S. Appl. No. 16/015,049.
USPTO; Non-Final Office Action dated Nov. 5, 2019 in U.S. Appl. No. 16/015,049.
USPTO; Notice of Allowance dated Feb. 20, 2020 in U.S. Appl. No. 16/015,049.
USPTO; Non-Final Office Action dated Oct. 2, 2020 in U.S. Appl. No. 16/073,693.

(56) References Cited

OTHER PUBLICATIONS

USPTO; Non-Final Office Action dated Apr. 13, 2020 in U.S. Appl. No. 16/070,133.
USPTO; Final Office Action dated Jan. 6, 2021 in U.S. Appl. No. 16/070,133.
USPTO; Restriction Requirement dated Sep. 19, 2019 in U.S. Appl. No. 16/073,706.
USPTO; Non-Final Office Action dated Oct. 24, 2019 in U.S. Appl. No. 16/073,706.
USPTO; Notice of Allowance dated May 11, 2020 in U.S. Appl. No. 16/073,706.
USPTO; Non-Final Office Action dated Jan. 10, 2020 in U.S. Appl. No. 16/076,673.
USPTO; Notice of Allowance dated Jun. 1, 2020 in U.S. Appl. No. 16/076,673.
USPTO; Non-Final Office Action dated Feb. 1, 2019 in U.S. Appl. No. 16/152,190.
USPTO; Notice of Allowance dated May 30, 2019, in U.S. Appl. No. 16/152,190.
USPTO; Restriction Requirement dated May 29, 2019 in U.S. Appl. No. 16/250,929.
USPTO; Notice of Allowance dated Oct. 23, 2019 in U.S. Appl. No. 16/250,929.
USPTO; Non-Final Office Action dated Jun. 30, 2020 in U.S. Appl. No. 16/477,106.
USPTO; Notice of Allowance dated Nov. 24, 2020 in U.S. Appl. No. 16/477,106.
USPTO; Restriction Requirement dated Apr. 8, 2020 in U.S. Appl. No. 16/479,257.
USPTO; Non-Final Office Action dated Jun. 30, 2020 in U.S. Appl. No. 16/479,257.
USPTO; Final Office Action dated Jan. 11, 2021 in U.S. Appl. No. 16/479,257.
USPTO; Non-Final Office Action dated Sep. 22, 2020 in U.S. Appl. No. 16/639,716.
USPTO; Final Office Action dated Mar. 15, 2021 in U.S. Appl. No. 16/639,716.
USPTO; Non-Final Office Action dated Dec. 30, 2020 in U.S. Appl. No. 16/652,672.
USPTO; Non-Final Office Action dated Jun. 2, 2020 in U.S. Appl. No. 16/684,338.
USPTO; Final Office Action dated Dec. 14, 2020 in U.S. Appl. No. 16/684,338.
USPTO; Non-Final Office Action dated Nov. 9, 2020 in U.S. Appl. No. 16/731,749.
USPTO; Non-Final Office Action dated Jun. 15, 2020 in U.S. Appl. No. 16/878,484.
USPTO; Notice of Allowance dated Dec. 7, 2020 in U.S. Appl. No. 16/878,484.
USPTO; Non-Final Office Action dated Dec. 15, 2020 in U.S. Appl. No. 16/831,722.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/018950.
PCT; International Search Report and Written Opinion dated Jul. 26, 2017 in Application No. PCT/US2017/017231.
PCT; International Preliminary Report on Patentability in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
PCT; International Search Report and Written Opinion in Application No. PCT/US2018/048873.
PCT; International Search Report and Written Opinion dated Jan. 18, 2019 in Application No. PCT/US2018/055264.
PCT; International Search Report and Written Opinion dated Jun. 9, 2020 in Application No. PCT/US2020/13218.
PCT; International Search Report and Written Opinion dated Aug. 6, 2020 in Application No. PCT/US2020/25068.
PCT; International Search Report and Written Opinion dated Sep. 4, 2020 in Application No. PCT/US2020/28004.
EP; European Search Report dated Jan. 30, 2019 in Application No. EP16815467.2.
CN; Notice of the First Office Action dated Sep. 2, 2019 in Chinese Application No. 201680049272.8.
EP; European Search Report dated Aug. 2, 2019 in Application No. EP16885434.7.
EP; European Search Report dated Aug. 2, 2019 in Application No. EP17745026.9.
CN; Notice of the First Office Action dated Sep. 30, 2019 in Chinese Application No. 201780020478.2.
EP; European Search Report dated Oct. 24, 2019 in Application No. 17757146.
PCT; International Preliminary Report on Patentability dated Oct. 29, 2019 in Application No. PCT/US2018/029382.
EP; European Search Report dated Jan. 29, 2020 in Application No. 17745013.7.
EP; European Search Report dated Jan. 29, 2020 in Application No. 17750776.1.
EP; European Search Report dated Feb. 7, 2020 in Application No. 17837566.3.
EP; European Search Report dated Mar. 6, 2020 in Application No. 17835231.6.
EP; European Search Report dated Jun. 18, 2020 in Application No. 16815467.2.
CN; Office Action dated Jun. 5, 2020 in Chinese Patent Application No. 2017800204782.
EP; European Search Report dated Jun. 26, 2020 in Application No. 17874229.2.
EP; European Search Report dated Sep. 30, 2020 in Application No. 17893481.6.
JP; Office Action dated Aug. 13, 2020 in Japanese Application No. 2017-566864.
CN; Office Action dated Aug. 14, 2020 in Chinese Patent Application No. 201680083636.4.
EP; European Search Report dated Nov. 19, 2020 in Application No. 18739158.6.
JP; Office Action dated Dec. 2, 2020 in Japanese Patent Application No. 2018-536737.
EP; European Search Report dated Dec. 23, 2020 in Application No. 18790713.4.
EP; European Search Report dated Dec. 14, 2020 in Application No. 18799263.1.
JP; Office Action dated Feb. 2, 2021 in Japanese Application No. 2018-539265.
Ahn et al., "Electrical Immunosensor Based on a Submicron-Gap Interdigitated Electrode and Gold Enhancement," Biosensors and Bioelectronics, vol. 26, pp. 4690-4696, (2011).

(56) References Cited

OTHER PUBLICATIONS

Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Ali et al., "DNA hybridization detection using less than 10-nm gap silicon nanogap structure," Sensors and Actuators A. vol. 199, pp. 304-309 (2013).
Antibody Structure Downloaded from https://absoluteantibody.com/antibody-resources/antibody-overview/antibody-structure/ (Mar. 1, 2019).
Argarana et al "Molecular cloning and nucleotide sequence of the streptavidin gene" Nucleic Acids Research, 1986, 14 (4): 1871-1882(1986).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).
Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces—Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).
Bornholt et al., "A DNA-Based Archival Storage System", Architectural Support for Programming Languages and Operating Systems, pp. 637-649 (2016).
Botsialas et al., "A Miniaturized Chemocapacitor System for the Detection of Volatile Organic Compounds," Sensors and Actuators B, Chemical, vol. 177, pp. 776-784, (2013).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74 (2002).
Cassie, A.B.D. et al., "Wettability of Porous Surfaces," Transitions of the Faraday Society, vol. 40, pp. 546-551, (Jan. 1944) (Abstract Only).
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen et al., "Electrochemical Approach for Fabricating Nanogap Electrodes with Well Controllable Separation," Applied Physics Letters, vol. 86, pp. 123105.1-123105.3, (2005).
Chen, X. et al., "Electrical Nanogap Devices for Biosensing," Materials Today, vol. 13, pp. 28-41, (2010).
Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).
Chen et al., "Fabrication of Submicron-Gap Electrodes by Silicon Volume Expansion for DNA-Detection," Sensors and Actuators A, vol. 175, pp. 73-77, (2012).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, J. E. et al., "Fabrication of Microchannel with 60 Electrodes and Resistance Measurement," Flow Measurement and Instrumentation, vol. 21, pp. 178-183, (2010) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (2016).
Gapin, A.I. et al., "CoPt Patterned Media in Anodized Aluminum Oxide Templates," Journal of Applied Physics, vol. 99(8), pp. 08G902 (1-3), (2006).
Ghindilis, A. et al., "Real Time Biosensor Platforms Fully Integrated Device for Impedimetric Assays," ECS Transactions, vol. 33, pp. 59-68, (2010).
Grass et al., "Robust Chemical Preservation of Digital Information on DNA in Silica with Error-Correcting Codes", Angewandte Chemie International Edition, vol. 54, No. 8, pp. 2552-2555 (2015).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
Hatcher et al., "PNA versus DNA: Effects of Structural Fluctuations on Electronic Structure and Hole-Transport Mechanisms," J. Amer. Chem. Soc., 130, pp. 11752-11761 (2008).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of the Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).

(56) References Cited

OTHER PUBLICATIONS

Iqbal et al., "Direct Current Electrical Characterization of ds-DNA in Nanogap Junctions," Applied Physics Letter, vol. 86, p. 153901-1-153901-3, (Apr. 2005).
Javey et al., "Layer-by-Layer Assembly of Nanowires for Three-Dimensional, Multifunctional Electronics," Nano Letters, vol. 7, pp. 773-777, (2007).
Khawli et al., "Charge Variants in IgG1-Isolation, Characterization, In Vitro Binding Properties and Pharmacokinetics in Rats," Landes Bioscience, vol. 2(6), pp. 613-623, (2010).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95 (2010) (Abstract Only).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Korlach et al., "Real-time DNA sequencing from single polymerase molecules," 11, Methods in Enzymology, Academy Press, vol. 472, pp. 431-455 (2010).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Li et al., "Graphene Channel Liquid Container Field Effect Transistor as pH Sensor," Hindawi Publishing Corp., Journal of Nanomaterials 2014.
Lin et al., "An Addressable Microelectrode Array for Electrichemical Detection," Analytical Chemistry, vol. 80, pp. 6830-6833, (2008).
Liu et al., "Controllable Nanogap Fabrication on Microchip by Chronopotentiometry," Electrochimica Acta, vol. 50, pp. 3041-3047, (2005).
Liu et al., "Atomically Thin Molybdenum Disulfide Nanopores with High Sensitivity for DNA Translocation," ACS Nano, vol. 8, pp. 2504-2511, (Feb. 18, 2014).
Liu et al., "An Enzyme-Based E-DNA Sensor for Sequence-Specific Detection of Femtomolar DNA Targets," J. Am. Chem. Soc., vol. 130(21), pp. 6820-6825, (2008).
MacNaughton et al., "High-Throughput Heterogeneous Integration of Diverse Nanomaterials on a Single Chip for Sensing Applications," PLOS One, vol. 9(10), e111377, 7 Pages, (2014).
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Nishida, et al. "Self-Oriented Immobilization of DNA Polymerase Tagged by Titanium-Binding Peptide Motif," Langmuir, vol. 31, pp. 732-740 (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).
Okinaka et al., ""Polymer" Inclusions in Cobalt-Hardened Electroplated Gold," Journal the of Electrochemical Society, vol. 125, p. 1745, (1978). (Abstract Only).
Park, S.J. et al., "Array-Based Electrical Detection of DNA with Nanoparticle Probes," Science, vol. 295, pp. 1503-1506, (Feb. 22, 2002).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005)(Abstract Only).
Parkin, I. P. et al., "Self-Cleaning Coatings," Journal of Materials Chemistry, vol. 15(17), pp. 1689-1695, (2004).
Paul et al., "Charge transfer through Single-Stranded Peptide Nucleic Acid Composed of Thymine Nucleotides," J. Phy. Chem. C 2008, 112, pp. 7233-7240 (2008).
Prins et al., "Room-Temperature Gating of Molecular Junctions Using Few-Layer Graphene Nanogap Electrodes," Nano Letters, vol. 11, pp. 4607-4611, (Oct. 21, 2011).
Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reed et al., "Conductance of a Molecular Junction Reports," Science, vol. 278, pp. 252-254, (Oct. 1997).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Reichert et al., "Driving Current Through Single Organic Molecules," Physical Review Letters, vol. 88(17), pp. 176804-1-176804-4, (Apr. 2002).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Ruttkowski, E. et al., "CMOS based Arrays of Nanogaps Devices for Molecular Devices," Proceedings of 2005 5th IEEE Conference on Nanotechnology, vol. 1, pp. 438-441, (2005) (Abstract Only).
Sanguino et al., "Interdigitated Capacitive Immunosensors with PVDF Immobilization Layers," IEEE Sensors Journal, vol. 14(4), pp. 1260-1265, (Apr. 2014).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Schaefer et al., "Stability and Dewetting Kinetics of Thin Gold Films on Ti, TiOx, and ZnO Adhesion Layers," Acta Materialia, vol. 61, pp. 7841-7848, (2013).
Schrott, W. et al., "Metal Electrodes in Plastic Microfluidic Systems," Microelectronic Engineering, vol. 86, pp. 1340-1342, (2009).
Shimanovsky et al., "Hiding Data in DNA," International Workshop on Information Hiding, Lecture Notes in Computer Science, pp. 373-386, (Dec. 18, 2012).
Shimoda, T. et al., "Solution-Processed Silicon Films and Transistors," Nature, vol. 440(7085), pp. 783-786, (Apr. 2006).
Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Sholders et al., "Distinct Conformations of a Putative Translocation Element in Poliovirus Polymerase," Journal of Molecular Biology, vol. 426(7), pp. 1407-1419, (Apr. 3, 2014).
Singh et al., "3D Nanogap Interdigitated Electrode Array Biosensors," Analytical and Bioanalytical Chemistry, vol. 397, pp. 1493-1502, (2010).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).

(56) References Cited

OTHER PUBLICATIONS

Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).

Stenning, "The Investigation of Grain Boundary Development and Crystal Synthesis of Thin Gold Films on Silicon Wafers," http://www.ucl.ac.uk/~ucapikr/projects, (Mar. 31, 2009).

Su, Y., "Modeling and Characteristic Study of Thin Film Based Biosensor Based on COMSOL," Mathematical Problems in Engineering, Article 581063 (6 Pages), (Apr. 7, 2014).

Thompson, "Solid-State Dewetting of Thin Films," Department of Materials Science and Engineering, vol. 42, pp. 399-434, (2012).

Urban, M. et al., "A Paralleled Readout System for an Electrical DNA-Hybridization Assay Based on a Microstructured Electrode Array," Review of Scientific Instruments, vol. 74, pp. 1077-1081, (2003) (Abstract Only).

Van Gerwin et al., "Nanoscaled Interdigitated Electrode Arrays for Biochemical Sensors," Sensors and Actuators B, vol. 49, pp. 73-80, (1998).

Van Megan et al., "Submicron Electrode Gaps Fabricated by Gold Electrodeposition at Interdigitated Electrodes," Key Engineering Materials, vol. 605, pp. 107-110, (2014).

Venkatramani et al., "Nucleic Acid Charge Transfer: Black, White and Gray," Coard Chem Rev., 255(7-8): pp. 635-648 (2011).

Wang et al., "Electronics and Optoelectronics of Two-Dimensional Transition Metal Dichalcogenides," Nature Nanotechnology, vol. 7, pp. 699-712, (Nov. 6, 2012).

Xu et al., "Fabrication of Complex Metallic Nanostructures by Nanoskiving," American Chemical Society Nano, vol. 1(3), pp. 215-227, (2007).

Yang et al., "Two-Dimensional Graphene Nanoribbons," J. Am. Chem. Soc. vol. 130, Issue 13 (2008).

Zafarani et al., "Electrochemical Redox Cycling in a New Nanogap Sensor: Design and Simulation," Journal of Electroanalytical Chemistry, vol. 760, pp. 42-47, (2015).

* cited by examiner

ENZYMATIC CIRCUITS FOR MOLECULAR SENSORS

CROSS-REFERENCE TO RELATED APPLICATIONS

This application is a continuation of U.S. patent application Ser. No. 16/878,484 filed May 19, 2020 and entitled "Enzymatic Circuits for Molecular Sensors", which is a divisional of U.S. patent application Ser. No. 16/684,338 filed Nov. 14, 2019 and entitled "Enzymatic Circuits for Molecular Sensors." The '338 application is a continuation of U.S. patent application Ser. No. 16/015,028 filed Jun. 21, 2018 (now U.S. Pat. No. 10,508,296) and entitled "Enzymatic Circuits for Molecular Sensors." The '028 Application is a continuation of PCT Application No. PCT/US18/29382, filed on Apr. 25, 2018 entitled "Enzymatic Circuits for Molecular Sensors," which claims priority to and the benefit of U.S. Provisional Patent Application Ser. No. 62/489,881 filed Apr. 25, 2017 and entitled "Enzymatic Circuits for Molecular Sensors," the disclosures of which are incorporated herein by reference in their entirety.

FIELD

The present disclosure is generally directed to molecular sensors and more particularly to molecular sensors in which an enzyme closes the circuit between two electrodes.

BACKGROUND

The broad field of molecular electronics was introduced in the 1970's by Aviram and Ratner. Molecular electronics achieves the ultimate scaling down of electrical circuits by using single molecules as circuit components. Molecular circuits comprising single molecule components can function diversely as switches, rectifiers, actuators and sensors, depending on the nature of the molecule. Of particular interest is the application of such circuits as sensors, where molecular interactions provide a basis for single molecule sensing. In particular, informative current changes could include an increase, or decrease, a pulse, or other time variation in the current.

Notwithstanding the achievements in the field of molecular electronics, new molecular circuits that can function as molecular sensors are still needed. In particular, the need still exists for improved single molecule systems that can yield molecular information with greater signal-to-noise ratios such that signals truly indicative of molecular interactions are distinguishable from non-informative noise.

SUMMARY

In various embodiments, single molecule enzyme-based circuits are disclosed wherein a single enzyme molecule is directly connected to a positive and negative electrode to form the circuit. These circuits are capable of yielding highly informative signals of enzyme activity. These improved signals have greater signal-to-noise levels such that the signals are more distinguishable from noise, and these improved signals include features that carry detailed information about the engagement between enzyme and the target substrate.

In various embodiments, a molecular sensor comprises an enzyme-based molecular circuit (conductive pathway) such as described herein. Such a sensor having a polymerase enzyme is usable to sense sequence information from a DNA template processed by the polymerase.

In various embodiments of the present disclosure, a molecular circuit is disclosed. The circuit comprises: a positive electrode; a negative electrode spaced apart from the positive electrode; and an enzyme connected to both the positive and negative electrodes to form a conductive pathway between the positive and negative electrodes.

In various aspects, the enzyme of the circuit may comprise a first wiring point connected to the positive electrode and a second wiring point connected to the negative electrode.

In various aspects, the circuit may further comprise at least one arm molecule having first and second ends, the first end bonded to the enzyme and the second end bonded to at least one of the electrodes, wherein the at least one arm molecule acts as an electrical wire between the enzyme and at least one of the electrodes.

In various aspects, the at least one arm molecule may be selected from the group consisting of a double stranded oligonucleotide, a peptide nucleic acid duplex, a peptide nucleic acid-DNA hybrid duplex, a protein alpha-helix, a graphene-like nanoribbon, a natural polymer, a synthetic polymer, and an antibody Fab domain.

In various aspects, at least one of the electrodes is connected to an internal structural element of the enzyme.

In various aspects, the internal structural element may be selected from the group consisting of an alpha-helix, a beta-sheet, and a multiple of such elements in series.

In various aspects, at least one of the electrodes may be connected to the enzyme at a location of the enzyme capable of undergoing a conformational change.

In various aspects, at least one arm molecule may comprise a molecule having tension, twist or torsion dependent conductivity.

In various aspects, the enzyme may comprise a polymerase.

In various aspects, the polymerase comprises *E. coli* Pol I Klenow Fragment.

In various aspects, the polymerase comprises a reverse transcriptase.

In various aspects, the polymerase comprises a genetically modified reverse transcriptase.

In various aspects, a molecular sensor comprises a circuit further comprising a positive electrode; a negative electrode spaced apart from the positive electrode; and a polymerase enzyme comprising *E. coli* Pol I Klenow Fragment connected to both the positive and negative electrodes to form a conductive pathway between the positive and negative electrodes, wherein the positive electrode and the negative electrode each connect to the polymerase at connection points within the major alpha-helix of the polymerase extending between amino acids at position 514 and 547.

In various aspects, a molecular sensor comprises a circuit further comprising a positive electrode; a negative electrode spaced apart from the positive electrode; and a polymerase enzyme connected to both the positive and negative electrodes to form a conductive pathway between the positive and negative electrodes, wherein the sensor is usable to sense sequence information from a DNA template processed by the polymerase.

In various aspects, a molecular sensor comprises a circuit further comprising a positive electrode; a negative electrode spaced apart from the positive electrode; and a polymerase enzyme connected to both the positive and negative electrodes to form a conductive pathway between the positive and negative electrodes, wherein the positive electrode and the negative electrode each connect to the polymerase at connection points on the thumb and finger domains of the polymerase, and wherein such points undergo relative motion in excess of 1 nanometer as the polymerase processes a DNA template.

In various aspects, the polymerase in this sensor is engineered to have extended domains which produce a greater range of relative motion as the polymerase processes a DNA template.

In various aspects, the polymerase in this sensor is engineered to have additional charge groups that variably influence the internal conduction path as the enzyme processes a DNA template.

In various aspects, the polymerase in this circuit is a genetically modified form of E. coli. Pol I, Bst, Taq, Phi29, or T7 DNA polymerases, or a genetically modified reverse transcriptase.

In various aspects, a molecular circuit comprises: a positive electrode; a negative electrode spaced apart from the positive electrode; and an enzyme connected to both the positive and negative electrodes to form a conductive pathway between the positive and negative electrodes, wherein the positive electrode and the negative electrode each connect to the enzyme at connection points in the enzyme comprising at least one of a native cysteine, a genetically engineered cysteine, a genetically engineered amino acid with a conjugation residue, or a genetically engineered peptide domain comprising a peptide that has a conjugation partner.

In various aspects, this circuit further comprises a gate electrode.

In various embodiments, a method of sequencing a DNA molecule is disclosed. The method comprises: providing a circuit further comprising a positive electrode; a negative electrode spaced apart from the positive electrode; and a polymerase enzyme connected to both the positive and negative electrodes to form a conductive pathway between the positive and negative electrodes; initiating at least one of a voltage or a current through the circuit; exposing the circuit to a solution containing primed single stranded DNA and/or dNTPs; and measuring electrical signals through the circuit as the polymerase engages and extends a template, wherein the electrical signals are processed to identify features that provide information on the underlying sequence of the DNA molecule processed by the polymerase.

In various embodiments, a method of molecular detection is disclosed. The method comprises, providing a circuit further comprising: a positive electrode; a negative electrode spaced apart from the positive electrode; a polymerase enzyme connected to both the positive and negative electrodes to form a conductive pathway between the positive and negative electrodes and a gate electrode; initiating at least one of a voltage or a current through the circuit; exposing the circuit to at least one of: a buffer of reduced ionic strength, a buffer comprising modified dNTPs, a buffer comprising altered divalent cation concentrations, specific applied voltage on the primary electrodes, a gate electrode voltage, or voltage spectroscopy or sweeping applied to the primary electrodes or gate electrode; and measuring an electrical change in the circuit.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures:

DETAILED DESCRIPTION

Figure 1:
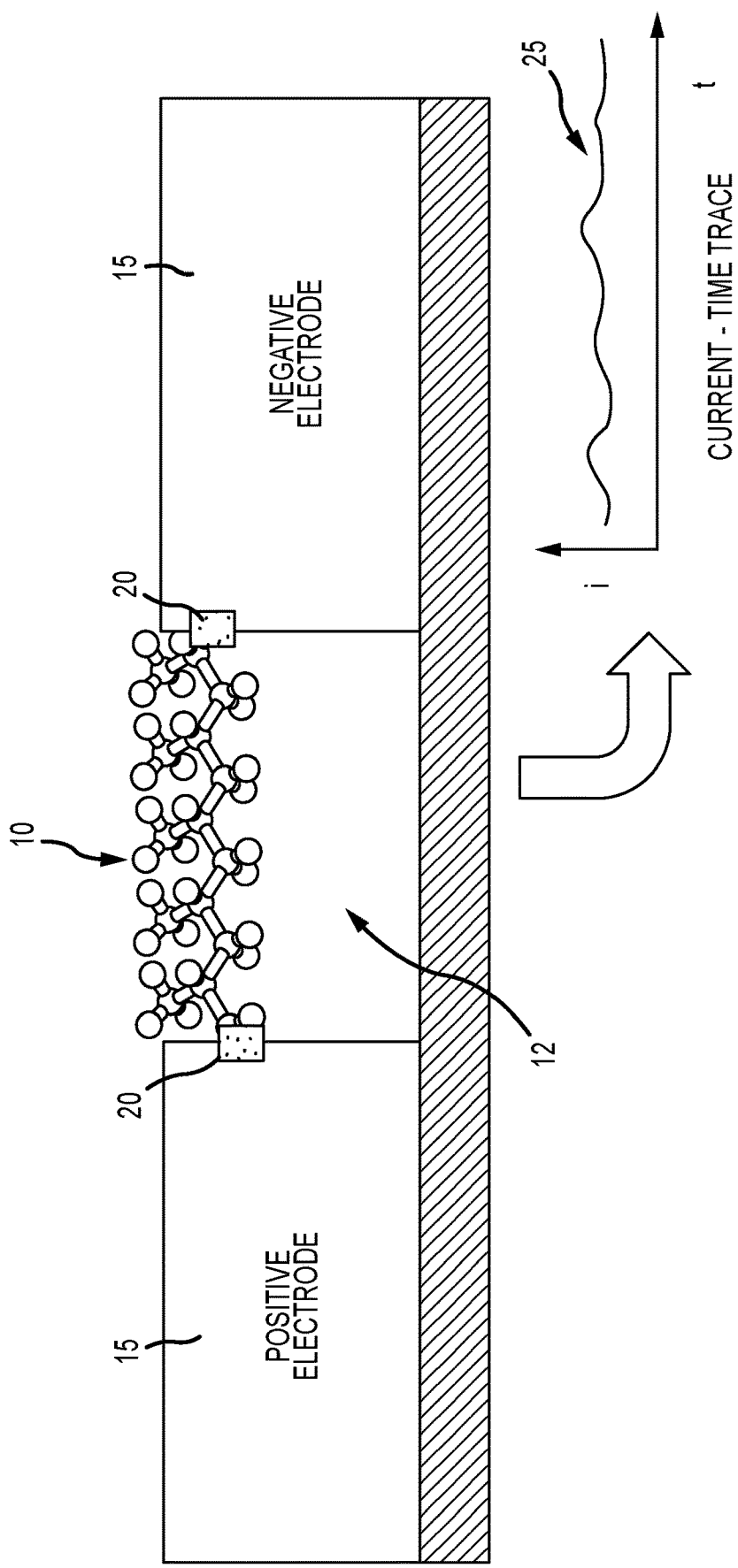
FIG. 1 illustrates the general concept of a molecular electronic circuit.

The detailed description of exemplary embodiments herein makes reference to the accompanying drawings, which show exemplary embodiments by way of illustration and their best mode. While these exemplary embodiments are described in sufficient detail to enable those skilled in the art to practice the inventions detailed herein, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, a molecular circuit is disclosed. The molecular circuit comprises: a positive electrode; a negative electrode spaced apart from the positive electrode; and an enzyme connected to both the positive and negative electrodes to form a conductive pathway between the positive and negative electrodes. In various examples, the enzyme comprises a first wiring point connected to the positive electrode and a second wiring point connected to the negative electrode.

Definitions and Interpretations

As used herein, the term "enzyme" means a molecule that acts to transform another molecule, by engaging with a variety of substrate molecules. Such transformation could include chemical modification, or conformational modification. Common biological enzyme classes are polymerases, ligases, nucleases, kinases, transferases, as well as genetically modified forms of these molecules. Polymerases herein include reverse transcriptases and any genetically modified reverse transcriptase, capable of directly acting on an RNA template. Enzymes are most commonly proteins, but may be composed of multiple amino acid chains, and may also be complexed with other types of molecules, such as RNA in the case of the ribosome enzyme.

As used herein, the term "substrate" for an enzyme refers to any of the molecules that the enzyme specifically engages with in the course of performing a transformation. For example, in the specific case of a DNA polymerase, the substrate consists of both a template DNA and dNTPs. In addition to the substrates of the enzyme, the enzyme may also complex with various co-factors that moderate its function or kinetics. For example, in the case of DNA polymerase, divalent cations such as Mg++ are often essential cofactors, but not considered as substrates.

As used herein, the term "dNTP" or "dNTPs" refers to any of the deoxynucleotide triphosphates involved in polymerase-based DNA synthesis, or that can be engaged for such DNA synthesis, including both native and modified forms of such molecules.

As used herein, the term "buffer" for an enzyme refers to a solution in which the enzyme is viable and functional, and typically containing the substrates and co-factors needed for enzyme activity. Such an enzyme buffer may typically comprise salts, detergents, and surfactants, singly or in various combinations, as well as specific cofactors, such as magnesium or other divalent cations for a polymerase enzyme, along with the substrates, such as DNA and dNTPs for a polymerase enzyme. Such a buffer herein may have its composition modified from standard forms, such as to enhance signal properties in a sensor exposed to the buffer.

As used herein, the term "electrode" means any structure that can act as an efficient source or sink of charge carriers. Most commonly these would be metal or semiconductor structures, such as those used in electronic circuits. A pair of spaced apart electrodes herein may comprise a source and drain electrode pair. In various embodiments of the present disclosure, a binding probe-based molecular circuit may further comprise a gate electrode. When present, a gate electrode is used to apply a voltage rather than transfer charge carriers. Thus it supports accumulation of charge carriers to produce a local electric field, but is not intended to pass current. A gate electrode will be electrically isolated from the primary conduction paths of the circuit by some form of insulating layer or material.

As used herein, the term "conjugation" means any of the wide variety of means of physically attaching one molecule to another, or to a surface or particle. Such methods typically involve forming covalent or non-covalent chemical bonds, but may also rely on protein-protein interactions, protein-metal interactions, or chemical or physical adsorption via intermolecular (Van der Waals) forces. There is a large variety of such methods know to those skilled in the art of conjugation chemistry. Common conjugation methods relevant to preferred embodiments herein include thiol-metal bonds, maleimide-cysteine bonds, material binding peptides such as gold binding peptides, and click chemistries.

As used herein, the term "initiating," in the context of an electrical parameter, is intended to be broader than the concept of "applying" an electrical value. For example, an electrical current may be initiated in a circuit. Such initiating of a current may be the result of applying a voltage to the circuit, but may be from other actions to the circuit besides applying a voltage. Further, a voltage may be initiated in a circuit. Such initiating of a voltage may be the result of applying a current to the circuit, but may be from other actions to the circuit besides applying an electrical current. In other examples, a voltage or a current may be initiated in one portion of a circuit as the result of applying a voltage or a current to the overall circuit. In a non-limiting example, a flow of electrons initiated from a negative to a positive electrode in a circuit of the present disclosure may be controlled by the voltage applied to the gate electrode of the circuit.

In various embodiments of the present disclosure, a molecular sensor comprises an enzyme connected to both a positive and a negative electrode to complete a circuit. Interactions of the enzyme with various substrates are detectable as changes in the current or other electrical parameter measured across the circuit. The present molecular sensor differs from the general concept of a molecular electronic circuit in that the enzyme is directly "wired" to both the positive and negative electrodes rather than bonded to a molecular bridge molecule that spans the gap between the electrodes to complete a circuit.

In various aspects of the disclosure, at least one of a voltage or a current is initiated in an enzyme-based molecular circuit. When a target interacts with the enzyme, electrical changes in the circuit are sensed. These electrical changes, or informative electrical signals, may include current, voltage, impedance, conductivity, resistance, capacitance, or the like. In some examples, a voltage is initiated in the circuit and then changes in the current through the circuit are measured as substrates interact with the enzyme. In other examples, a current is initiated in the circuit, and changes to voltage in the circuit are measured as substrates interact with the enzyme. In other examples, impedance, conductivity, or resistance is measured. In examples wherein the circuit further comprises a gate electrode, such as positioned underneath the gap between the positive and negative electrodes, at least one of a voltage or current may be applied to the gate electrode, and voltage, current, impedance, conductivity, resistance, or other electrical change in the circuit may be measured as substrates interact with the enzyme.

FIG. 1 illustrates the general concept of a molecular electronic circuit having a bridge molecule 10 attached to and bridging the gap 12 between electrodes 15, as well as some type of conjugation group 20 or other mechanism that binds the molecule to the electrodes (depicted as small shaded squares). FIG. 1 further illustrates that a current, (i), may pass through this molecule and be measured versus time, (t), as shown in the inset plot 25.

Figure 2:
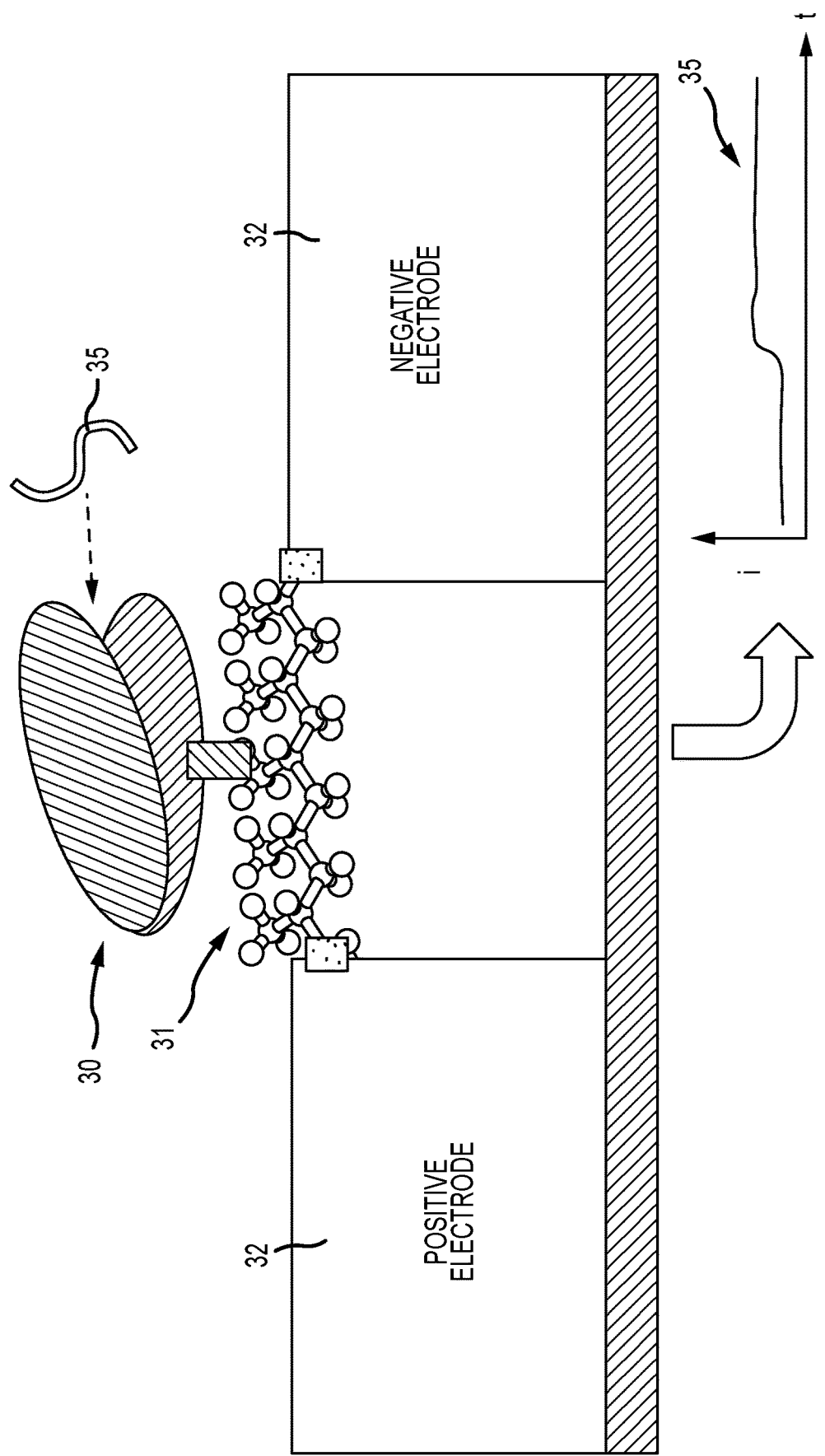
FIG. 2 illustrates the general concept of engaging an enzyme to a molecular electronic circuit, such as to act as a sensor of enzyme activity with its target.

FIG. 2 illustrates a molecular electronic sensor in which an enzyme 30 is conjugated to the molecular bridge component 31 spanning the electrodes 32, wherein monitoring the current provides a sensor for the enzyme engaging with and processing its target substrate 35 when exposed to a suitable buffer solution. In such a sensor system, the local charge perturbations that result from the target substrate engaging with the enzyme perturb charge transport through the primary bridge component, and are thus registered as a change in conductivity or current versus time, as indicated by the step-up change in the current (i) vs. time (t) current plot inset 38 in FIG. 2.

In contrast to the general molecular circuit concept as depicted in FIGS. 1 and 2, in various embodiments of the present disclosure a molecular sensor comprises a single enzyme molecule directly wired into the circuit path, such that all electrical current passing through the molecular circuit must flow through the enzyme. Thus the enzyme is an essential conduction path in the circuit, like an electronic component on a circuit board. The present concept is illustrated generally in FIG. 3, which shows an enzyme 42 connected between molecular arms 40. By forcing all current in the circuit to pass through the enzyme, the current carriers are forced to pass closer to the precise location of electrochemical interactions between the enzyme and target substrate 45, thereby causing such interactions to have greater impact on the current carriers, and, in turn making the overall current more sensitive to the details of these interactions. This is illustrated schematically by the current versus time, (i vs. t), plot inset 50 in FIG. 3, wherein the current step is shown to be much larger than that produced by the configuration of FIG. 2, and also includes additional features not present in a current versus time plot such as depicted in FIG. 2. The higher current step provides improved signaling. Related methods and preferred embodiments herein promote improved signaling of enzyme-based molecular sensors. Further, the configuration of the enzyme as an essential conduction path is fundamentally different from the common configuration of FIG. 2, in which there are many conduction paths that do not pass through the enzyme, and where potentially none of the charge carriers actually traverse the enzyme, and where there is no means provided to direct charge carriers to pass near key active sites within the enzyme.

In various embodiments, the enzyme may be coupled to both positive and negative electrodes at two or more points, such as to ensure that charge carriers traversing the molecular structure pass into and out of the enzyme.

Figure 3:
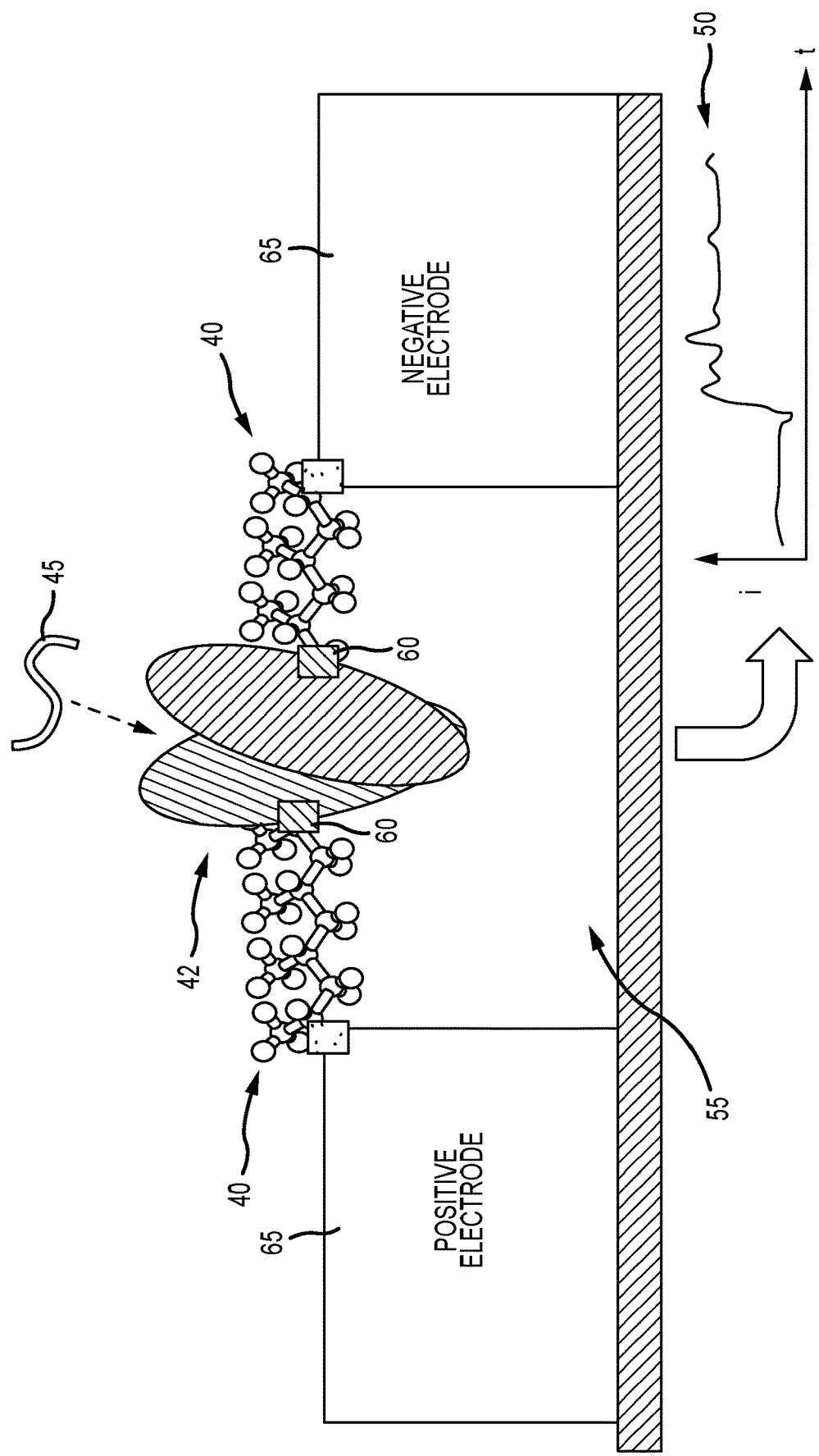
FIG. 3 illustrates an enzyme that is wired directly into the current path, in accordance with various embodiments.

As shown in the embodiment of FIG. 3, two molecular arms are conjugated to the enzyme to provide physical anchors and entry and exit paths for the current through the enzyme. Such arms may comprise any convenient molecule that provides a conducting connection or semi-conducting connection between the enzyme and the electrodes. Further, molecular arms may provide spanning length extensions, to help span a larger electrode gap 55 that is wider than the 3D structure of the enzyme. Such arms may also provide the advantage of keeping the enzyme away from contacting the electrodes 65 where unfavorable or damaging interactions may occur with the electrodes, such as a denaturing adsorption to the electrode. Such arms may also provide for more compatible or efficient coupling to the electrodes, such as by coupling to the electrodes via chemical groups that are not readily found or made available on the enzyme. For example, in one specific embodiment, the electrode comprises gold and the molecular arm includes a thiol group, such that the arm couples to the gold electrode via well-known thiol-gold binding. Thus the molecular arm accomplishes the binding while the enzyme may not have such available thiol groups. Or, in another embodiment, the arms may present a click-chemistry binding group, for coupling to electrodes that are derivatized with the cognate binding partners for the click chemistry.

In various embodiments, molecular arms comprise some form of conjugation 60 to the enzyme, as well as their conjugations or couplings to the electrodes. Many conjugation chemistries can be employed for this purpose. In a non-limiting example, such conjugation comprises chemical crosslinking, which can preferentially couple suitable chemical groups on the arms to amino acid residues on the enzyme. In various embodiments, a maleimide group on the arm couples to a surface cysteine on the enzyme. In other aspects, genetically modified versions of an enzyme may be created and employed, such as enzymes comprising specific amino acids or protein domains engineered into their amino acid structure that provide specific conjugation sites. For example, cysteine amino acids engineered at specific sites on the enzyme provide for the attachment point of arms that present a maleimide group. Two such cysteine sites conjugate to two maleimide derivatized arms to produce a configuration such as that shown in FIG. 3. In this case, one or more native cysteines that would provide competing arm binding sites may be "engineered out" of the amino acid sequence. If not all such sites can be removed, it is possible to use various purification methods from synthetic chemistry to isolate desired enzyme-arm conjugates from unwanted configurations. In other variations, genetic methods are used to engineer into the amino acid sequence of the enzyme amino acids comprising residues that uniquely conjugate to a cognate group on the arms. This variation includes cases where non-standard amino acids are employed, such as amino acids modified to present a click-chemistry group, via protein expression systems that use a modified genetic code and modified transfer RNAs to put non-native amino acids at specific sequence sites in an expressed enzyme protein.

In other embodiments, a peptide domain that specifically binds with a cognate group on the arms is engineered into the sequence of a protein enzyme. In one such embodiment, a peptide that is an antigen to an antibody is engineered into the enzyme, and the Fab binding domain of the antibody is used on the arms. One such embodiment is to use the FLAG peptide motif DYKDD, and any suitable ANTI-FLAG Fab domain. Any other peptide antigens and their cognate Fab domains can similarly be used to conjugate arms to specific sites in an engineered enzyme protein, by engineering the peptide antigen into the desired conjugation sites on the enzyme. Other such peptide domains make use of the SPY-TAG/SPY-CATCHER protein-protein binding system, by engineering either the SPY-TAG domain or the SPY-CATCHER domain into the enzyme protein, and placing the cognate domain in the arms. When engineering such peptide binding domains into the enzyme, another embodiment is to add short linker peptide sequences flanking the target peptide, to enhance the availability of the domain for binding. Such short linkers may comprise short glycine and serine rich linkers, as are known to those skilled in the art of protein engineering, including, but not limited to, the linker amino acid sequences G, GS, GSG, GGSG, etc.

In various examples, the arm molecules comprise any molecules that provide for conduction of charge carriers into and out of the enzyme. In certain embodiments, such arms comprise molecular wires from the many forms known in field of molecular electronics, functionalized with suitable conjugation and binding groups for wiring to electrodes and enzyme. In various aspects, such arms may comprise single stranded DNA, double stranded DNA, peptides, peptide alpha-helices, antibodies, Fab domains of antibodies, carbon nanotubes, graphene nanoribbons, natural polymers, synthetic polymers, other organic molecules with p-orbitals for electron delocalization, or metal or semiconductor nanorods or nanoparticles. In further embodiments, the arms may comprise double stranded DNA with thiol-bearing groups at one end, and maleimide at the other end that couples to the enzyme, or a peptide alpha-helix with a cysteine or gold binding peptide at one termini, and a maleimide at the other end that couples to the enzyme, or a graphene nanoribbon with thiol-bearing groups at one end, and a maleimide bearing group at the other end that couples to the enzyme. In certain embodiments, the two arm molecules used to couple an enzyme to two electrodes are identical molecules, and in other embodiments, the two arm molecules are different molecules. In some examples, there may be a "positive electrode" arm and a "negative electrode" arm, providing for oriented binding of an enzyme to the corresponding "positive" and "negative" electrodes in FIG. 3.

Figure 4:
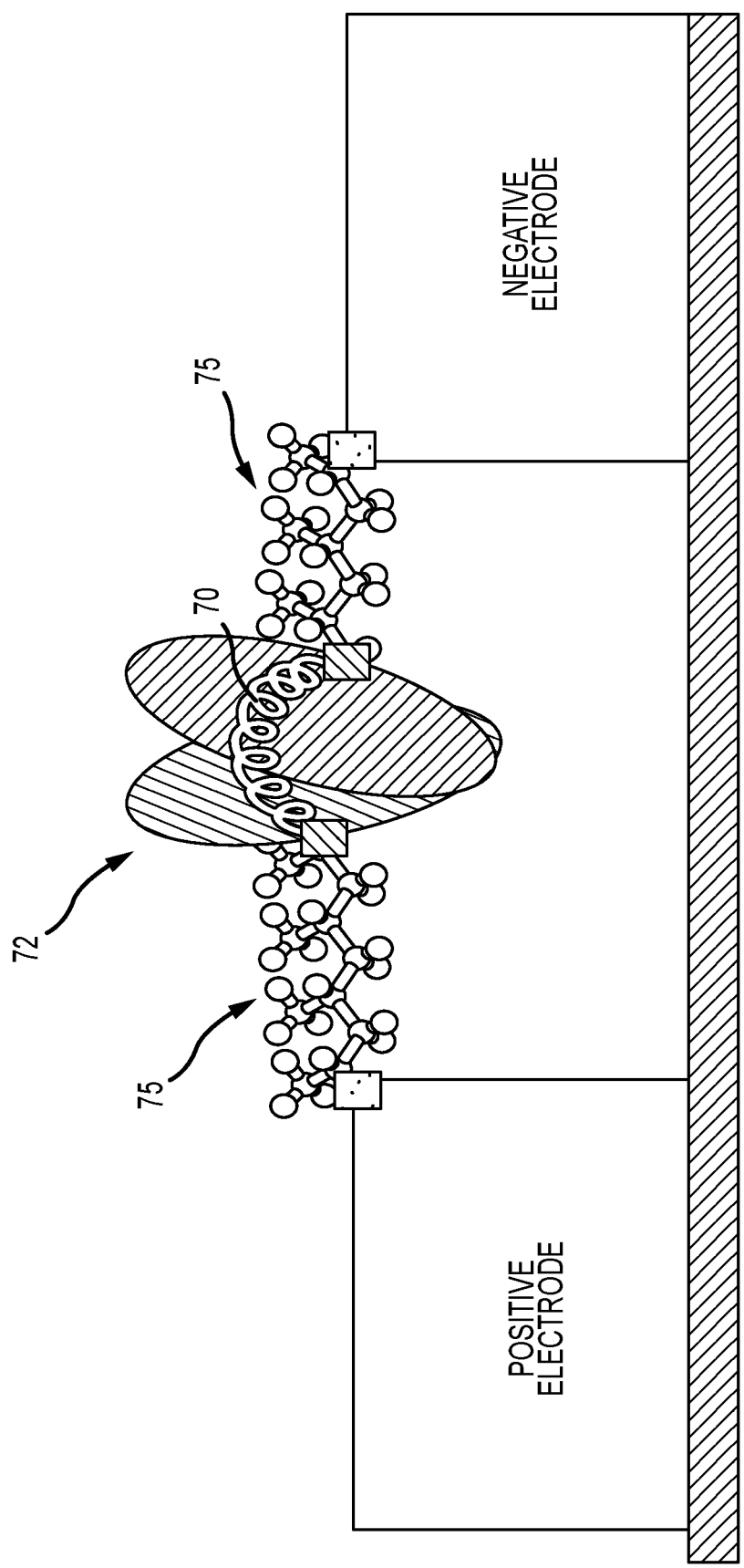
FIG. 4 illustrates an enzyme that is wired directly into the current path, with the connection made to an internal alpha-helix structure within the enzyme, in accordance with various embodiments.
Figure 5:
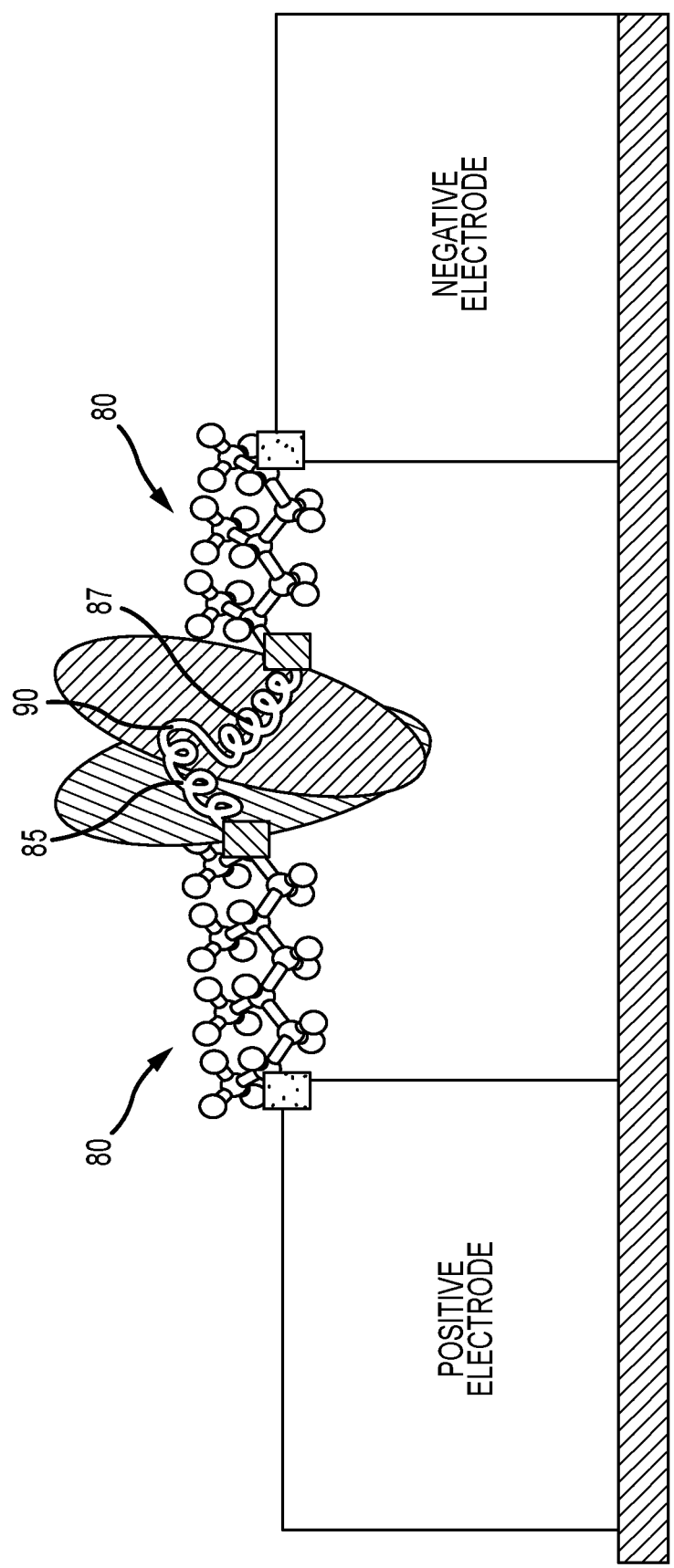
FIG. 5 illustrates an enzyme that is wired directly into the current path, with the connection made to a series of two or more internal alpha-helix structures in series within the enzyme, in accordance with various embodiments.
Figure 6:
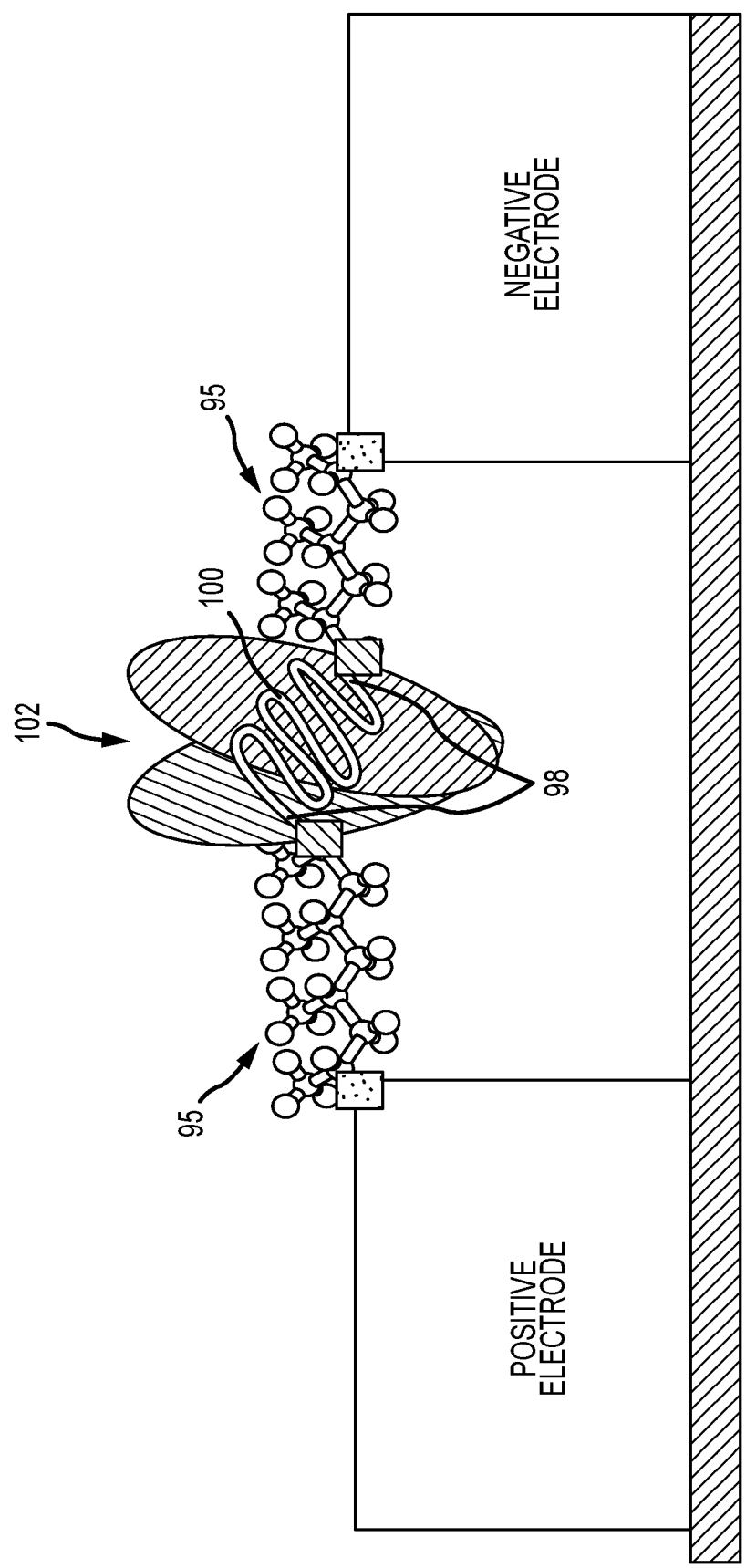
FIG. 6 illustrates an enzyme that is wired directly into the current path, with the connection made to an internal beta-sheet structure within the enzyme, in accordance with various embodiments.

In various embodiments, arm conjugation points connect directly to specific protein structural elements within the enzyme. A non-limiting example is illustrated in FIG. 4, where the arms 75 are shown wired directly to an alpha-helix structure 70 in the enzyme 72. Such structural elements provide preferential conduction paths through the enzyme. Direct wiring to natural conduction paths in the enzyme guide current closer to active regions of interest within the enzyme, such as substrate binding pockets, and may thereby provide for further enhanced current signals, or current signals that carry more information on enzyme-substrate interactions. For example, one embodiment is shown in FIG. 4, where the arms wire directly to an alpha-helix that spans between two points on or near the surface of the enzyme. Another example is shown in FIG. 5, where the arms 80 wire directly to two alpha-helices (the first alpha-helix 85 and the second alpha helix 87) that appear in series internally in the enzyme, with a single connecting loop 90 separating them. Yet another embodiment is shown in FIG. 6, where the arms 95 wire directly to two points 98 on a beta-sheet 100 internal to the enzyme 102.

In general, a protein enzyme will have a 3D structure that includes well known secondary structural elements such as alpha-helices and beta-sheets. These are primarily hydrogen bonded structures that can provide discrete conduction paths through the body of the enzyme, to the extent that current carriers, such as electrons, may efficiently hop along such structures, or along the hydrogen bonds that define such structures, with less resistance than otherwise hopping or tunneling off such structures. These structures provide preferential conduction paths that will channel charge carriers, and by selecting such structures, charge is forced to pass close to active regions of the enzyme, and current-based sensing of the activity will be improved. Having the arms directly connected to such structures, or within a small number of amino acids of the termini of such structures, the current flowing along these desirable paths is maximized, and thus the desirable signals that come from the current along such paths is maximized. In this way, current going elsewhere within the enzyme is minimized, and thus the noise from probing these less informative regions is also minimized.

In various examples, the wiring can be to such structures that appear in the enzyme "in series", such as for example, two alpha-helices in series as indicated in FIG. 5, or a beta-sheet in series with an alpha-helix, or three successive alpha-helices. In general, each successive element in series appears in the enzyme primary amino acid sequence as separated from the previous element by a small number of amino acids, such 0, 1, 2, or up to approximately 10 amino acids, which typically form a connecting loop in the secondary structure. Wiring of elements in series may also be achieved by wiring to structures that are not contiguous in the primary amino acid sequence of the enzyme, but are nonetheless spatially contiguous and in conductive contact, and form a preferred conduction path, owing to hydrogen bonding, salt bridges, disulfide bridges, or other types of molecular interaction that establish secondary, tertiary or quaternary protein structure and that can provide a clearly defined and favorable conduction path from one structural element (beta-sheet, alpha-helix) to another. These structural elements of interest for wiring, either in isolation or in series, are most evident when examining the 3D structure of the proteins involved, as can be observed from the crystal structures, and in particular, by examination of the protein structures obtained by X-ray or NMR crystallography. This useful form of structural information is illustrated by the polymerase enzyme structure shown in FIG. 12.

Figure 7:
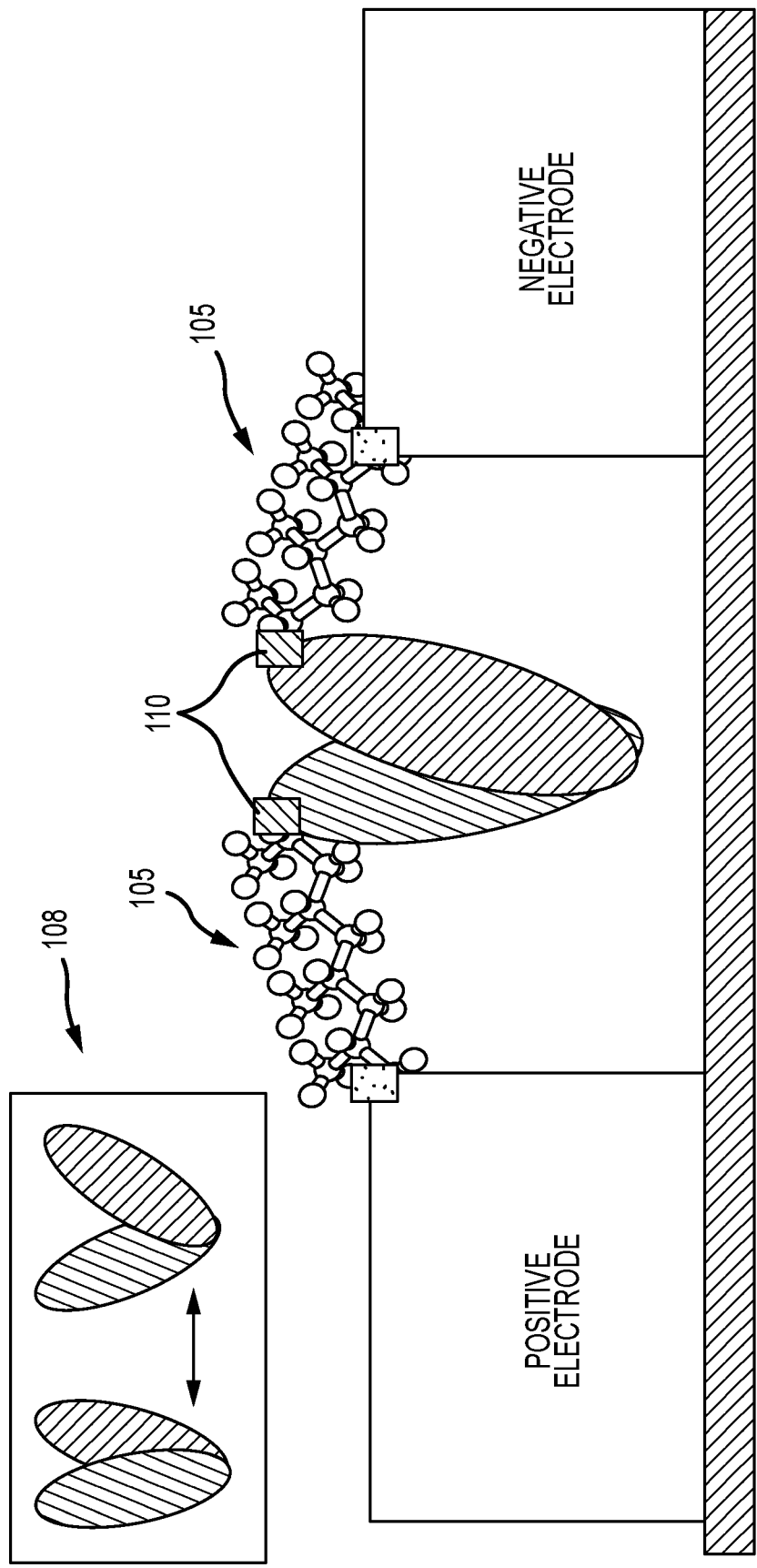
FIG. 7 illustrates an enzyme that is wired directly into the current path, such that connections are made to points of conformational change in the enzyme, to induce tension changes into the circuit during enzyme activity.

In other embodiments, the arms are wired to points on the enzyme that undergo conformation changes or relative motion during enzyme function, such as illustrated in FIG. 7. In this case, the arms 105 are wired to two points 110 that are indicated as having relative motion, as illustrated in the inset 108, during enzyme activity. This configuration can enhance signaling by several means. First, such motions can change the tension in the arms, and it is known that tension changes in molecules can change their conductivity, thus the motion may be transduced via tension into a change in conductivity of the arms, which consequently show up in the current signals. In this way, the current may contain information about the conformational changes in the enzyme. Second, similarly, this configuration can cause tension in the enzyme as it changes conformation, and thus alter conductivity of the enzyme. Since the enzyme is an essential current path, the conformation changes would transduce into current changes, and thereby represent conformation information in the sensing current. This configuration could also enhance signaling by altering the conformational changes of the enzyme, which may in some situations lead to an enhanced signal, for either a native enzyme, or one engineered to specifically benefit from such conformation-sensitive wiring. In one embodiment, an enzyme is engineered to have extended regions that undergo greater conformational change or relative motion (e.g. as demonstrated by extending the length of the two tips of the scissor-shaped enzyme indicated in FIG. 7), so as to enhance the range of motion, and therefore the range of tension changes in the arms and enzymes.

In other aspects, conformational changes in the enzyme, such as when induced binding occurs between the enzyme and a substrate, are translated into a twist, torque or rotation of at least one arm, and that twist, torsion or rotation alters the conductivity of the arm. One such example is an arm comprising an organic polymer further comprising polycyclic aromatic rings, such as polythiophene or polyphenylene, whereby previously lined up p-orbitals are rotated out of alignment by C—C bond rotation when the arm is twisted, torqued or rotated in response to an enzyme conformational change. When the arm is twisted, torqued or rotated, the electrons have impeded delocalization through the organic polymer. In certain embodiments, such impeded flow may act on only a subset of the charge carriers, depending on, for example, the polarization or other quantum state of the charge carrier, such as spin polarization of an electron charge carrier, or the momentum or energy state of the charge carrier.

Figure 8:
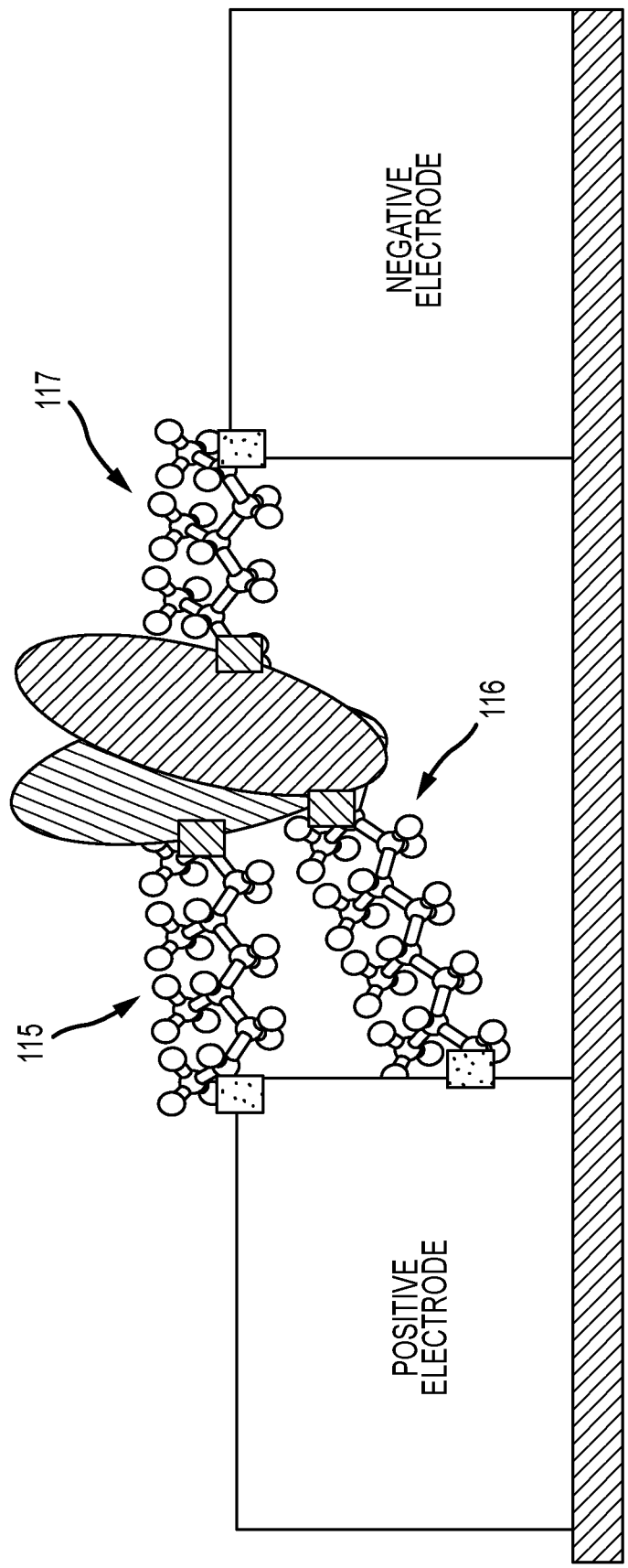
FIG. 8 illustrates an enzyme that is wired directly into the current path, with additional connections made to stabilize the position of the enzyme.

Another example is illustrated in FIG. 8, wherein the molecular sensor circuit comprises more than two arms, for example, 3 arms (the first arm 115, the second arm 116, and the third arm 117). The benefits to using additional enzyme wiring points and associated arms include addition of other desirable conduction paths through the enzyme, and increasing the overall conduction through the enzyme. Such additional arms may also provide stabilization, impose a spatial orientation (such as to orient an active site), or otherwise reduce physical degrees of freedom or conformational entropy, which may improve sensing by reducing the variability in conduction that comes from the system having more accessible conformations. Such additional arms may be conductive, but they can also be insulating if they are present primarily to provide stability, orientation, or reduction in spatial degrees of freedom. Such additional arms may connect to the electrode, or to other portions of the structure, such as to a substrate supporting the electrodes. Such arms may connect to additional electrodes in a system comprising more than two electrodes, including the case of a system with a gate electrode, such as a buried gate electrode. Connection to a gate electrode may refer to connection to the conductive portion of the gate, or connection to the insulating layer that separates actual conductive gate from the circuit, or, in the case of a buried gate, the surface layer above the buried gate, such as the connection to the surface illustrated in FIG. 16.

Figure 9:
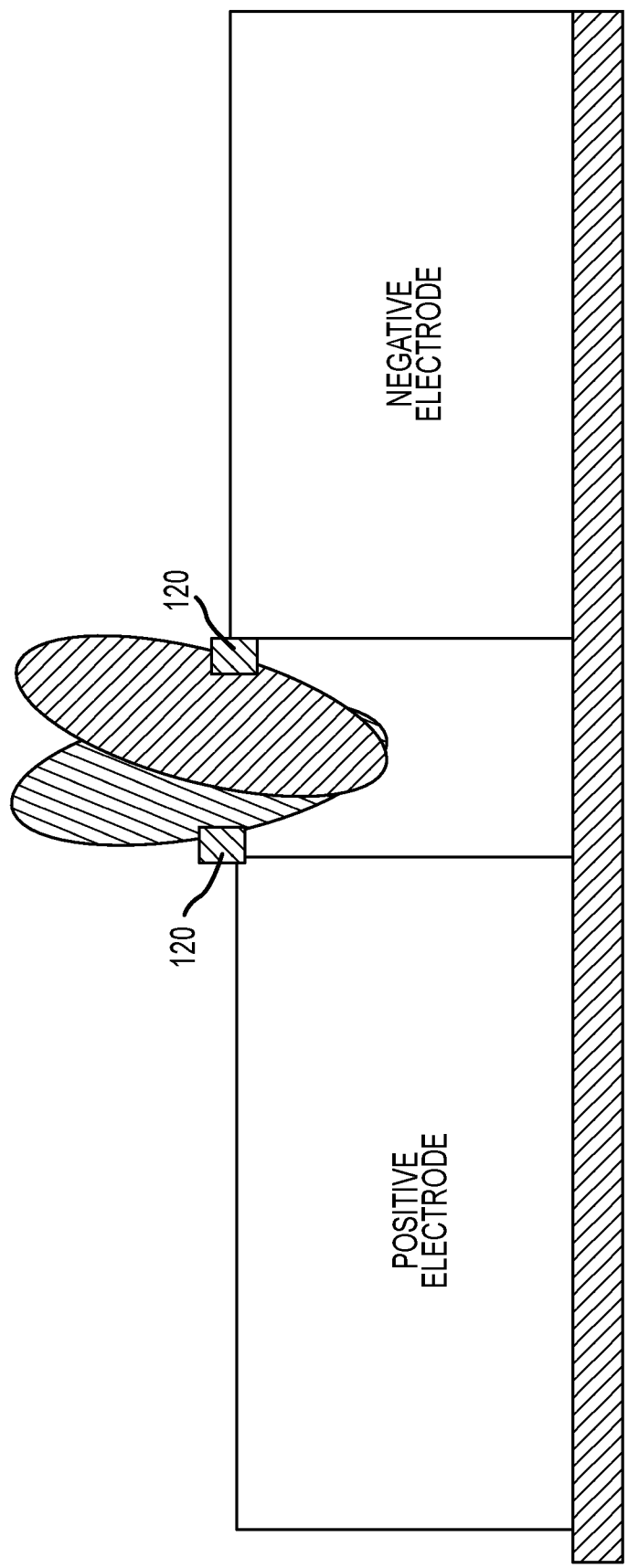
FIG. 9 illustrates a schematic of an enzyme directly wired into the current path of a circuit, in accordance with various embodiments, wherein the enzyme directly couples to the electrodes without the use of arm molecules.

As illustrated in FIG. 9, the enzyme may be connected to the electrodes directly 120, as an essential conduction path, without the use of arm molecules. In this case, groups on the enzyme directly couple to the electrodes. Or, in another embodiment, one wiring connection comprises direct coupling to the enzyme, the other via an arm molecule. The advantages of this arm-less configuration include minimizing the length of the conduction path, since the parts of the conduction path outside of the enzyme can be sources of unwanted noise, resistance or capacitance. The considerations above for the case of wiring with arms generally also apply to the special case of an arm-less configuration as well as the configuration of a single arm combined with direct enzyme coupling. Specifically, in embodiments lacking arms, the enzyme may still be wired via internal structures, or at points of conformational change.

A sensor comprising a directly wired enzyme as an essential conduction path may have its signal performance enhanced through various environmental factors. For example, the choice of buffer, buffer additives, temperature and applied voltage may be modulated to improve the signal quality. In particular, since enzymes may complex with various cofactors that modulate their kinetics, and the salt levels in the buffer also impact enzyme kinetics, as does temperature, these factors may be used to improve signaling performance. In addition, the overall ionic strength of the buffer solution defines the Debye length in the solution, that is the distance over which electric fields extend in solution, and can impact the extent to which current carriers passing through the enzyme are influenced by the charge distributions of the enzyme and substrate, and thus buffer ionic strength or total salt concentration is another means of influencing or enhancing the signaling. In embodiments utilizing a polymerase enzyme, the divalent cation content of the buffer is known to influence enzyme activity, and the choice of divalent cation, for example from among Mg++, Mn++, Ni++, Zn++, Co++, Ca++, Cr++, and their concentration may be optimized to improve the signaling from a polymerase wired as an essential conduction path.

The applied driving voltage may be optimized to improve the signaling from an enzyme wired as an essential conduction path. Based on energy barriers within the enzyme, certain voltages may lead to improved signaling performance. In addition to an applied voltage, various embodiments may also have a gate electrode, such as a buried gate below the lower substrate indicated in FIG. 3, such that voltages applied to the gate electrode further modulate the signaling properties of the enzyme circuit. Certain embodiments may employ voltage spectroscopy, wherein the driving or gate voltages are swept through a range of values, and the signal of interest is in the response from this sweep, which contains information on the interaction between the enzyme and its substrates.

Figure 10:
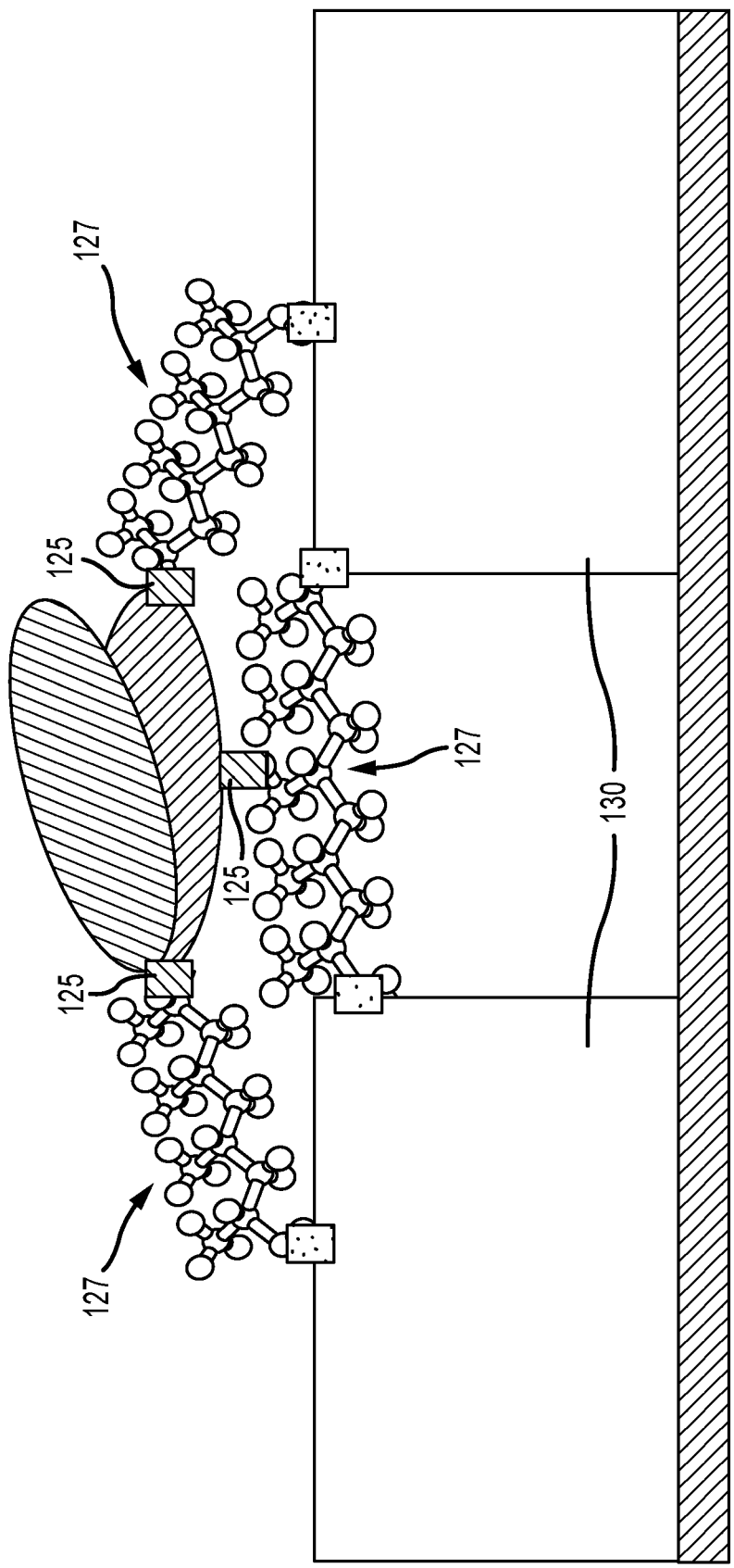
FIG. 10 illustrates a schematic of an enzyme directly wired by two points of contact into a circuit, as well as also having a one-point conjugation to a molecular wire, utilizing one pair of electrodes to measure the combined conduction, in accordance with various embodiments.
Figure 11:
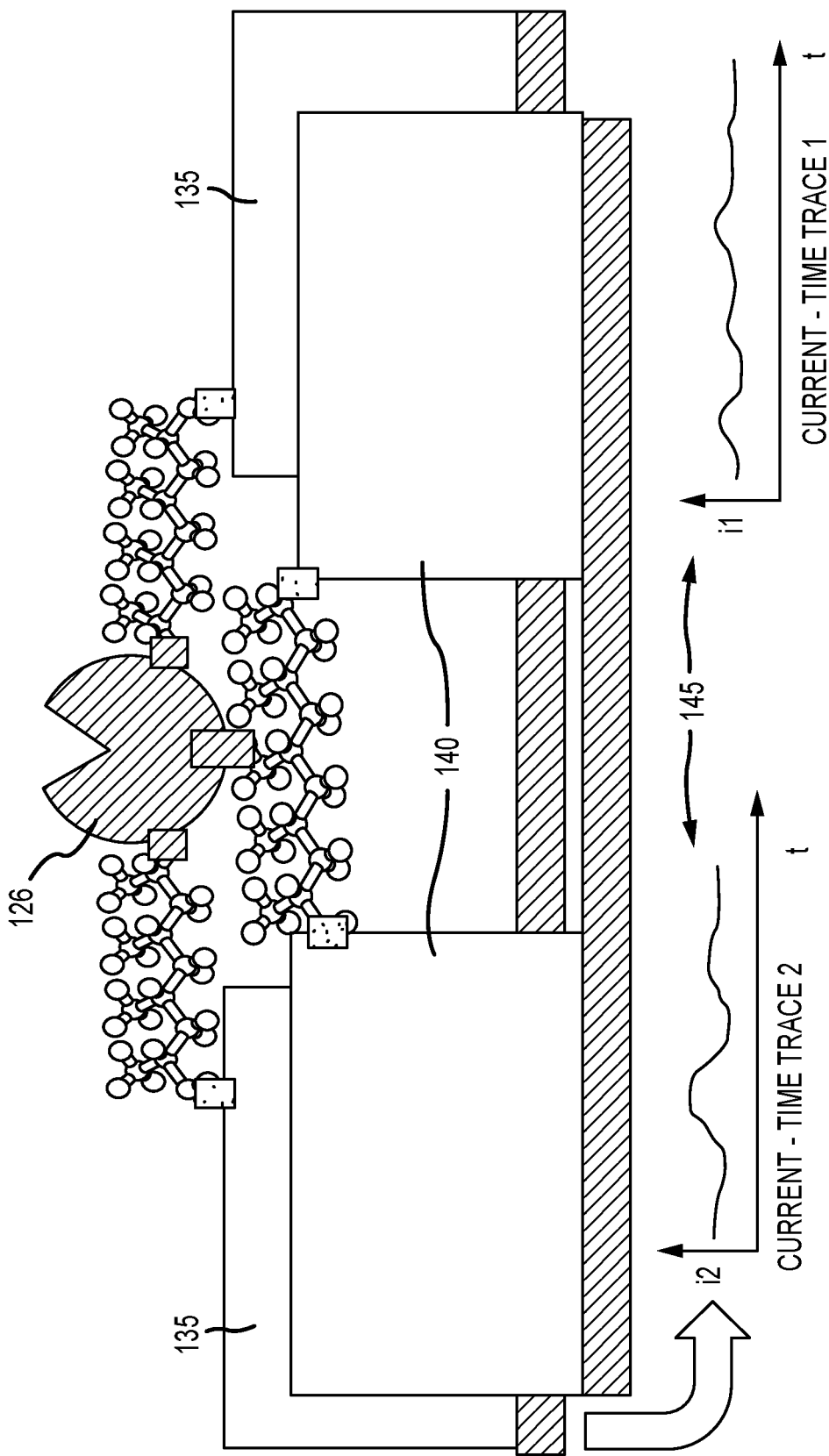
FIG. 11 illustrates a schematic of an enzyme directly wired by two points of contact into a circuit, as well as also having a one-point conjugation to a molecular wire, utilizing two pairs of electrodes to measure these two modes of conduction independently, in accordance with various embodiments.

In general, the molecular circuit sensors of the present disclosure comprise the wiring of an enzyme with at least two points of electrical contact, so as to make the enzyme an essential conduction path, in contrast to the configuration of FIG. 2. Two-point wiring of the enzyme may be combined with a conjugation 125 to one or more molecular arms 127, as shown in FIGS. 10 and 11. In these embodiments, the current can be both driven through the enzyme, for sensing, and the enzyme can also modulate current through the other molecular wire, as an additional sensing mode. In FIG. 10, these conduction modes are monitored by a single electrode pair 130, and combine to produce a single current, whereas in FIG. 11, these two conduction modes can be monitored by two separate electrode pairs (a first electrode pair 135 and a second electrode pair 140), producing two current measurements 145. In certain embodiments, the sensor may comprise an enzyme 126 wired up with two or more points of contact as a conduction path, in conjunction with additional sensor configuration features. Wiring the enzyme at two points, with input and output electrical contacts, can provide enhanced signaling. Other possible and non-limiting configurations are illustrated in FIGS. 10 and 11.

Figure 12:
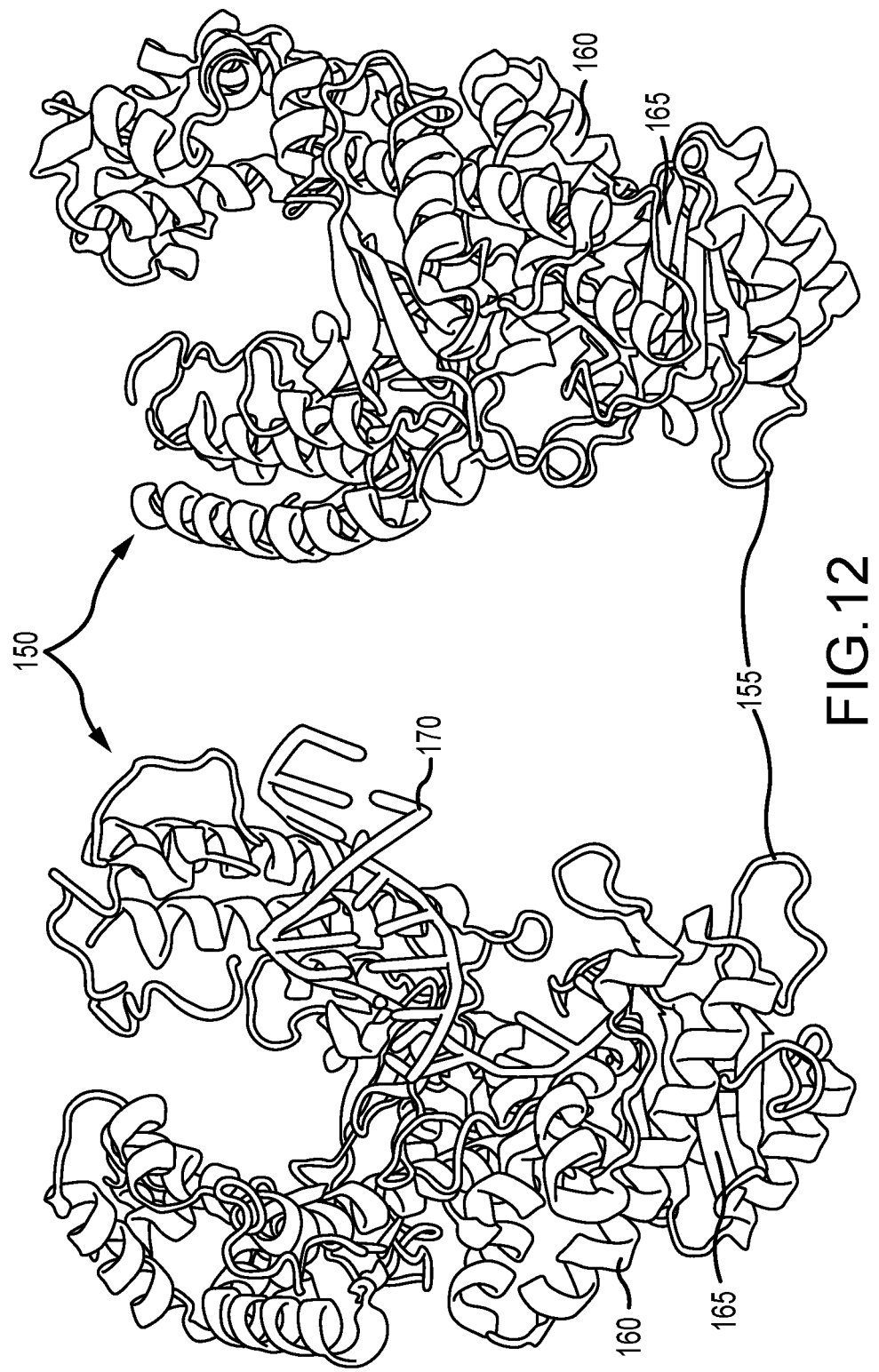
FIG. 12 illustrates a protein structure view of the E. coli Pol I Klenow Fragment Polymerase enzyme, illustrating the presence of alpha-helix, beta-sheet, and connecting loop structures.

In various embodiments, a molecular circuit sensor comprises a polymerase enzyme. FIG. 12 shows a representative polymerase enzyme 150, the Klenow Fragment of *E. coli* DNA Polymerase I. FIG. 12 illustrates a ribbon diagram of the enzyme structure, from two different views, with the enzyme engaged with a double-stranded DNA template 170.

The enzyme primary structure is a single amino acid sequence of 605 amino acids. The secondary structure and tertiary structure of the enzyme are depicted in FIG. 12. This figure shows the structural elements of the enzyme. In particular, there are 28 distinct alpha-helix elements 160, and two major beta-sheet elements 165, separated by short flexible loop segments 155. Such structural elements are similarly present in other types of polymerases and other enzyme proteins in general. In the course of enzyme activity, these structural features engage in electrical, chemical, mechanical and conformational perturbations, and wiring to these features within an electrical circuit can transduce these perturbations into measured signals.

Figure 13:
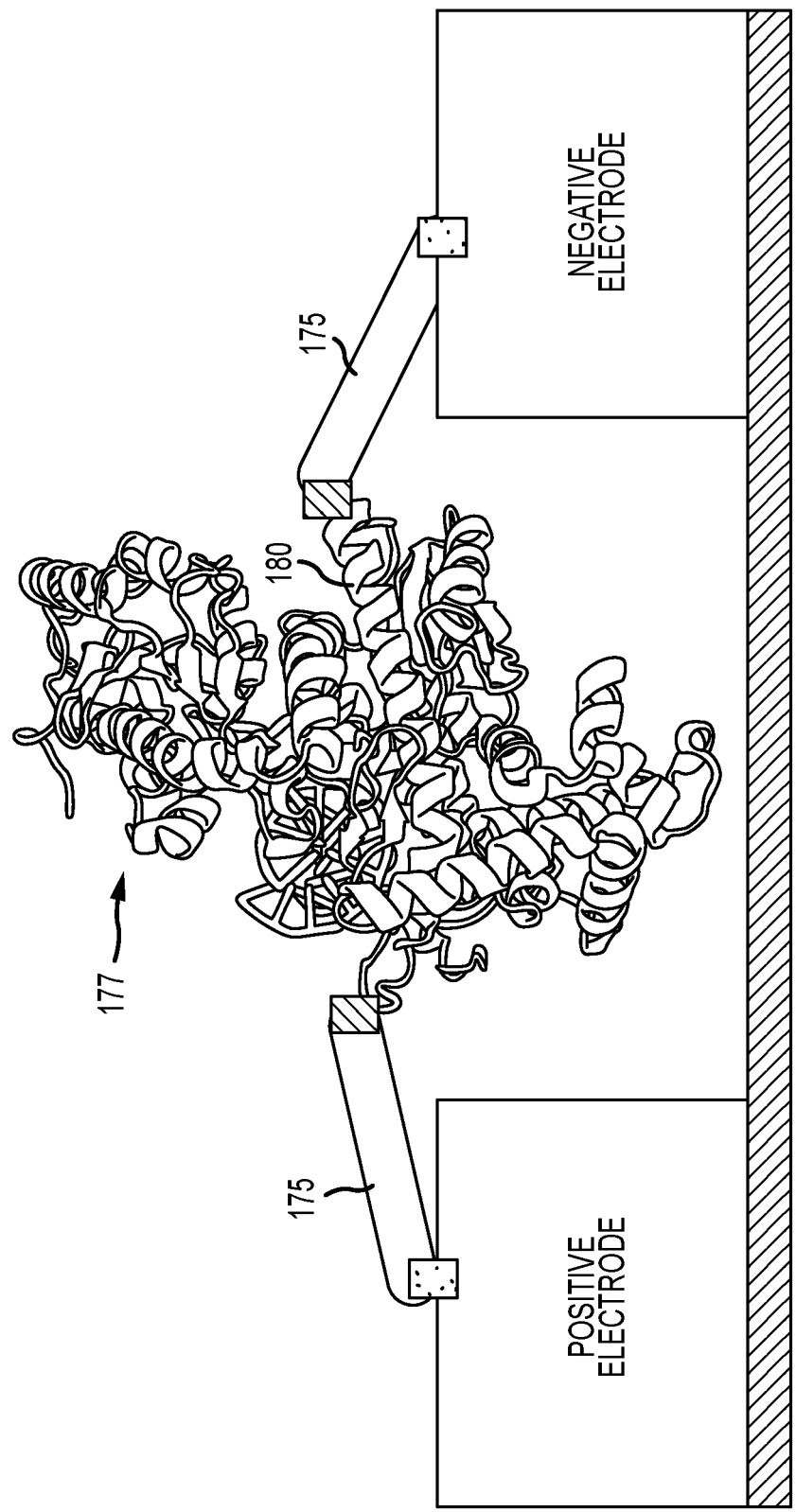
FIG. 13 illustrates a schematic of a polymerase enzyme directly wired into the current path of a circuit, in accordance with various embodiments, wherein a specific alpha-helix is used for the contacts, and molecular arms provide coupling to the electrodes.

FIG. 13 shows an embodiment where the polymerase 177 is wired as an essential conduction path, and specifically wired to the ends of a long alpha-helix 180 that passes through the center of the enzyme. This alpha-helix was chosen because it passes very near to the active pocket of the polymerase, and therefore can provide for enhanced current sensing of the polymerase activity as it binds to a primed strand and extends the primer through incorporation of dNTPs. Other alpha-helices in the structure will provide other sensing opportunities, and other embodiments comprise wiring to such alpha-helix structures, or the beta-sheet structures, or other such structures occurring in series. The arms 175 indicated in FIG. 13 may comprise double stranded oligonucleotides terminated with a maleimide, which couples to a cysteine genetically engineered into a precise location in a mutant form of the polymerase. In another embodiment, the arms comprise a protein alpha-helix terminated with a maleimide which couples such a cysteine. One specific embodiment of such a mutant polymerase includes cysteine (C) placed at the conjugation points indicated in FIG. 3, which arise from replacing the glutamine (Q) at amino acid position 548 by C, and replacing the serine (S) at amino acid position 508 by C, and these two locations lie just outside and bracket a single long (37 amino acid) alpha-helix that extends from amino acid position 514 to 547. In certain embodiments, the mutant polymerase further has the single native C at amino acid position 584 replaced by a non-cysteine, such as S, so as to provide exactly the two sites for coupling of the maleimide terminated arms, via the well-known maleimide-cysteine conjugation. Making such amino acid substitutions to introduce cysteines should be done in a manner that does not alter highly conserved amino acids (as conserved in comparison to other polymerases), does not alter amino acids in the alpha-helix or other structural elements that are the target of the wiring, does not alter amino acids directly participating in critical enzyme function, such as those that interact directly with the structure of the substrate binding pocket, the DNA substrate or the dNTP substrates. Similar selection principles apply to other enzymes as well when mutating in cysteine as a maleimide conjugation point.

Figure 14:
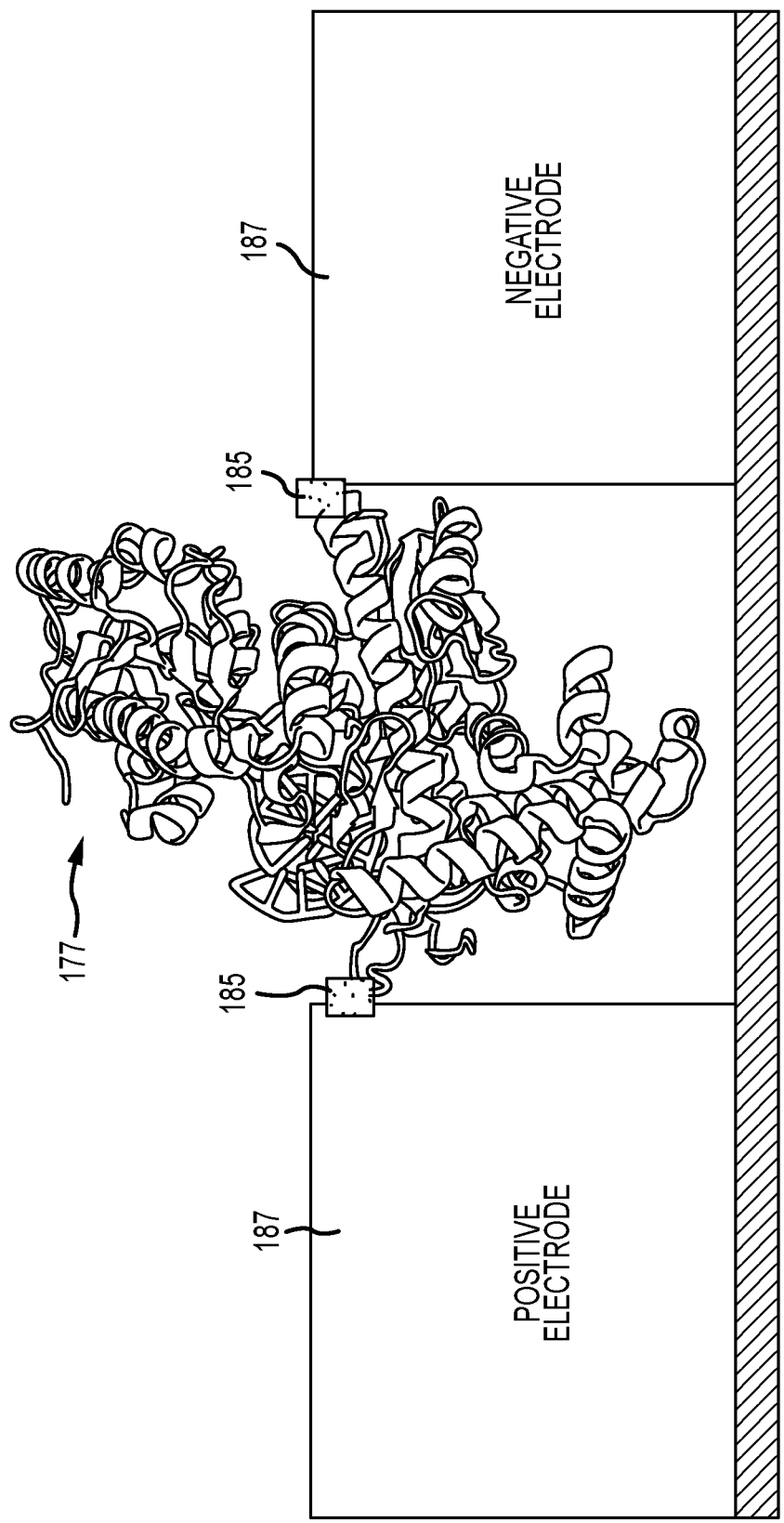
FIG. 14 illustrates a schematic of a polymerase enzyme directly wired into the current path of a circuit, in accordance with various embodiments, wherein a specific alpha-helix is used for the contacts, and the polymerase directly couples to the electrodes without the use of arm molecules.

FIG. 14 illustrates an alternative embodiment where the mutant polymerase 177 of FIG. 13 is directly conjugated 185 to the electrodes 187, coupling to the internal alpha-helix, without the use of connecting arms. This coupling can be achieved, for example, by utilizing gold electrodes, and a gold-binding peptide (GBP) with a maleimide terminus, such that the maleimide conjugates the GBP to the mutant polymerase at the cysteine sites described above, and the GBP conjugates to the gold electrode, thereby wiring in the polymerase via these two cysteine sites. Other embodiments of direct maleimide-mediated conjugations to the electrodes are enabled by using conjugating groups having the form X-maleimide bonded to the cysteines on the polymerase, such that X is a group that then binds to the electrode surface.

Figure 15:
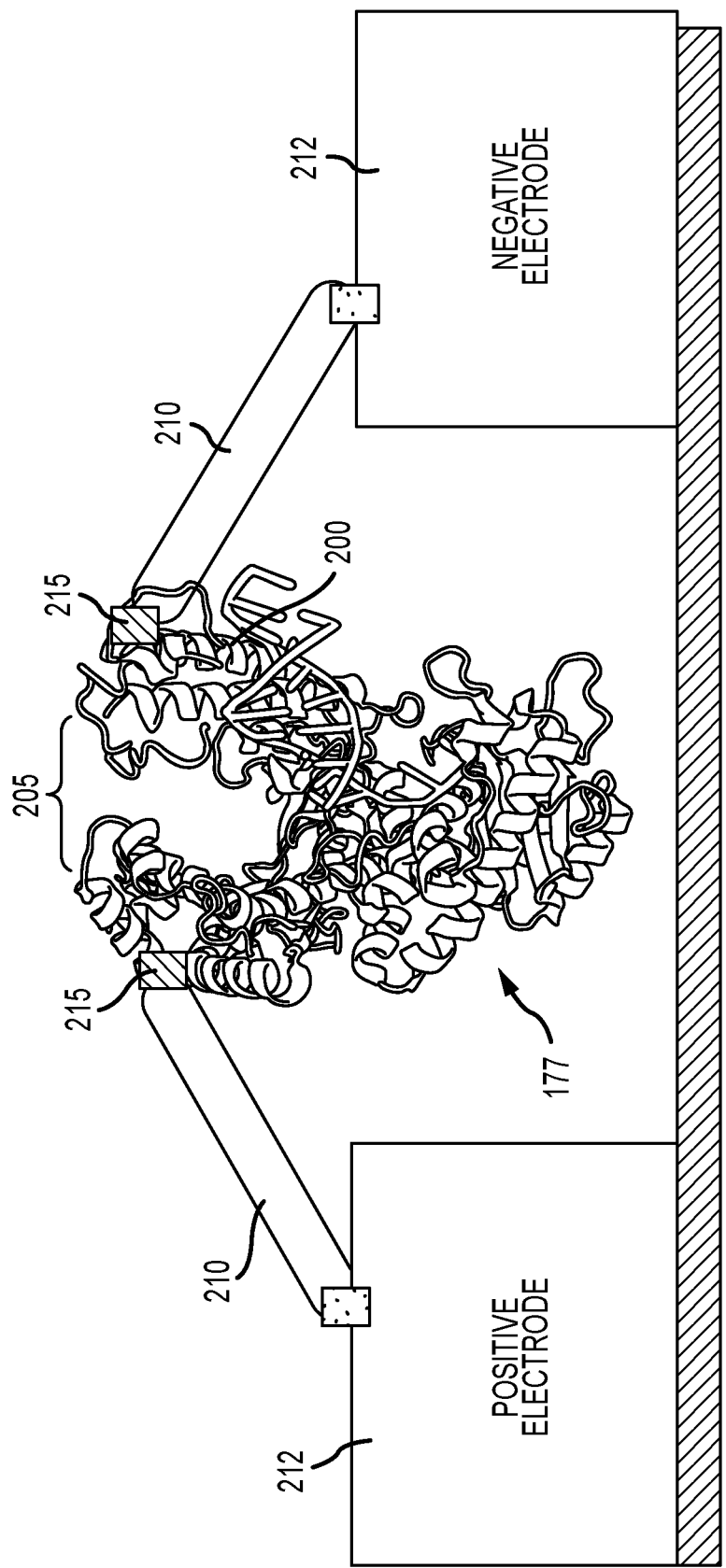
FIG. 15 illustrates a schematic of a polymerase enzyme directly wired into the current path of a circuit, in accordance with various embodiments, wherein arms are wired to the points that undergo relative motion when the finger and thumb domains change relative conformation.

FIG. 15 illustrates an alternative embodiment, where the mutant polymerase 177 of FIG. 13 is wired to the electrodes 212 using connecting arms 210 through an alpha-helix 200 adjacent to the binding cleft 205 of the polymerase. The connecting arms are wired to two points 215 on the polymerase. In embodiments, these two points have the ability to move relative to each other, thereby allowing for changes in conductivity and enhanced signaling.

Figure 16:
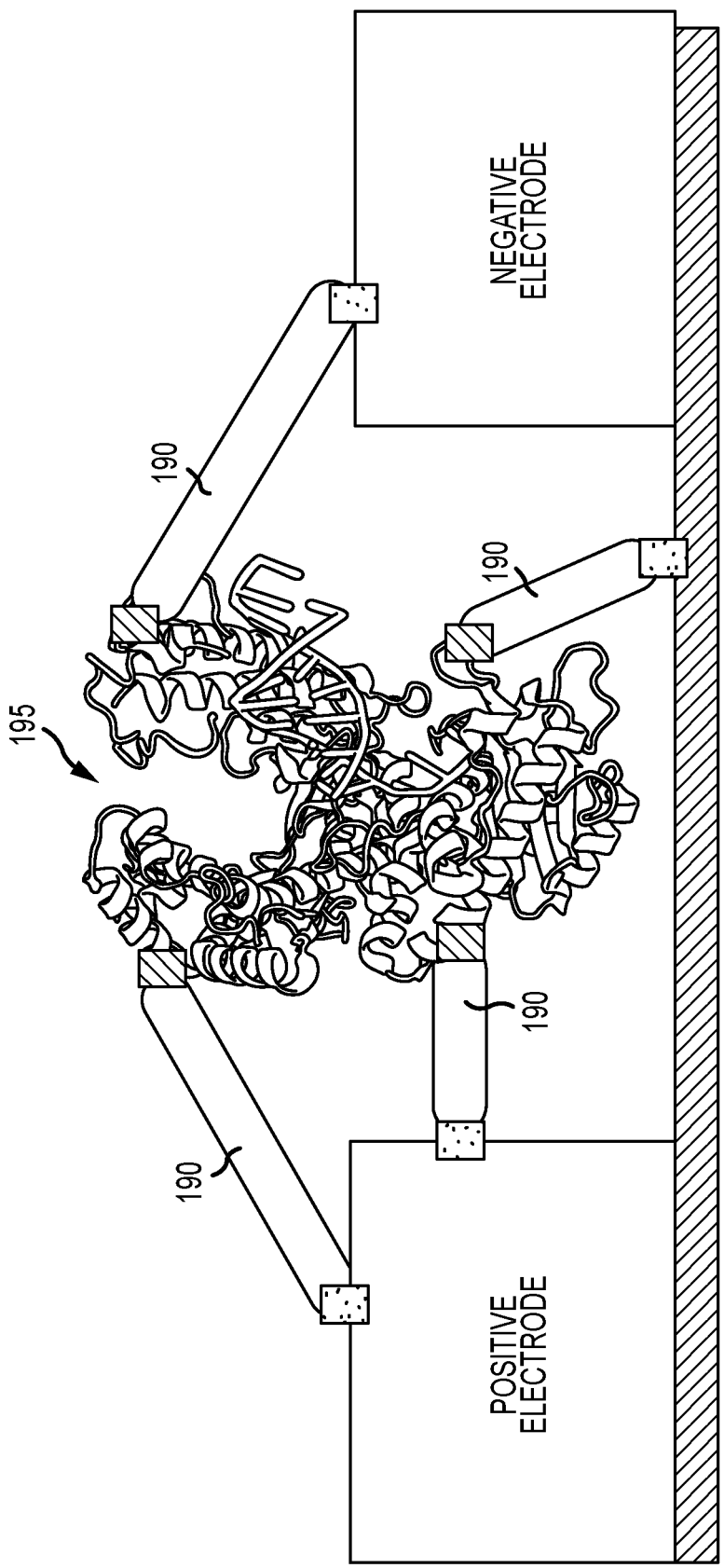
FIG. 16 illustrates a schematic of a polymerase enzyme directly wired into the current path of a circuit, and where additional connecting arms are wired to provide stabilization and fixed spatial orientation.

FIG. 16 illustrates an embodiment in which multiple arms 190 are used to wire up the polymerase 195 as an essential conducting path, as well as to stabilize its position and orientation relative to the electrodes and substrate. The lower pair of arms indicated can be either conducting or insulating, in accordance with various embodiments.

In various embodiments, a circuit comprises an enzyme wired in as an essential conduction path. The circuit may comprise first and second wiring points, connecting to a first and a second electrode such as a positive electrode and a negative electrode.

In various embodiments, the circuit may further comprise at least one arm molecule having two ends, one end bonded to the enzyme and the other end bonded to at least one of the electrodes, wherein the at least one arm molecule acts as an electrical wire between the enzyme molecule and at least one of the electrodes. Such an arm molecule may be selected from the group consisting of a double stranded oligonucleotide, a peptide nucleic acid (PNA) duplex, a PNA-DNA hybrid duplex, a protein alpha-helix, a graphene-like nanoribbon, a natural polymer, a synthetic organic molecule e.g. a synthetic polymer, and an antibody Fab domain. In other examples, the enzyme is wired directly to the electrodes without the use of any arm molecules. The wiring may be to an internal structural element in the enzyme, such as an alpha-helix, or a beta sheet, or multiple such elements in series.

In various embodiments, a circuit comprises an enzyme wired at points that undergo relative conformational change. In certain aspects, arms comprise molecules that have a tension dependent conductivity. In other examples, arm molecules may have torsion or twist dependent conductivity. Additional wiring points may be used to couple the enzyme at additional sites.

In various embodiments, a circuit comprises a polymerase enzyme, such as for example, *E. coli* Pol I Klenow Fragment, wherein the wiring is to the major alpha-helix extending between amino acids at position 514 and 547. Such connection may rely on the placement of genetically engineered cysteines at or near these amino acid positions. Circuits comprising a polymerase may be used to sense sequence information from a DNA template processed by the polymerase.

A circuit in accordance to various embodiments of the present disclosure may be exposed to a solution containing primed single stranded DNA, and/or dNTPs, wherein the current through the circuit is measured as the polymerase engages and extends a template, and the resulting signals are processed to identify features that provide information on the underlying sequence of the DNA molecule processed by the polymerase.

The connection between the enzyme molecule and at least one of the positive electrode and negative electrode may comprise any one of: a native cysteine, a genetically engineered cysteine, a genetically engineered amino acid with a conjugation residue, or a genetically engineered peptide domain comprising a peptide that has a conjugation partner. In certain aspects, the wiring is to points on the thumb and finger domain of the enzyme, where such points undergo relative motion in excess of 1 nm as the polymerase processes a DNA template. In other aspects, the polymerase is engineered to have extended domains that produce a greater range of relative motion as the polymerase processes a DNA template. For example, conformational changes in an enzyme may be accentuated by extending various domains in the enzyme. A polymerase enzyme may also be engineered to have additional charge groups that variably influence the internal conduction path as the enzyme processes a DNA template.

In various embodiments, a circuit is exposed to a solution comprising modified dNTPs that variably influence the internal conduction path as the enzyme processes a DNA or RNA template. In some cases, the polymerase enzyme is a genetically modified form of one of: E. coli. Pol I polymerase, Bst polymerase, Taq polymerase, Phi29 polymerase, T7 polymerase, and reverse transcriptase. In other examples, a circuit is exposed to one or more of the conditions of: a buffer of reduced ionic strength, a buffer comprising modified dNTPs, a buffer comprising altered divalent cation concentrations, specific applied voltage on the primary electrodes, a gate electrode voltage, or voltage spectroscopy or sweeping applied to the primary electrodes or gate electrode.

In various embodiments, the polymerase enzyme comprises a reverse transcriptase or genetically modified reverse transcriptase, capable of directly acting on an RNA template. Use of a reverse transcriptase in these circuits has the benefit that the reverse transcriptase can directly process an RNA template, and therefore provide a means for directly sequencing RNA molecules. In various aspects, this reverse transcriptase could be any monomeric reverse transcriptase or a genetically modified form thereof, such as Moloney murine leukemia virus reverse transcriptase, porcine endogenous retrovirus reverse transcriptase, bovine leukemia virus reverse transcriptase, mouse mammary tumor virus reverse transcriptase, or a heterodimeric reverse transcriptase such as human immunodeficiency virus reverse transcriptase or Rous sarcoma virus reverse transcriptase.

In certain examples, a method of sequencing a DNA molecule is disclosed. The method comprises: providing an enzyme-based molecular circuit having spaced-apart positive and negative electrodes and a polymerase enzyme molecule connected to both the positive and negative electrodes to form a conductive pathway between the electrodes; initiating at least one of a voltage or a current through the circuit; exposing the circuit to a solution containing primed single stranded DNA and/or dNTPs; and measuring electrical signals through the circuit as the polymerase engages and extends a template, wherein the electrical signals are processed to identify features that provide information on the underlying sequence of the DNA molecule processed by the polymerase.

In other aspects, a method of molecular detection is disclosed. The method comprises: (a) providing an enzyme-based molecular circuit having spaced-apart positive and negative electrodes, a polymerase enzyme molecule connected to both the positive and negative electrodes to form a conductive pathway between the electrodes, and a gate electrode; (b) initiating at least one of a voltage or a current through the circuit; (c) exposing the circuit to at least one of: a buffer of reduced ionic strength, a buffer comprising modified dNTPs, a buffer comprising altered divalent cation concentrations, specific applied voltage on the primary electrodes, a gate electrode voltage, or voltage spectroscopy or sweeping applied to the primary electrodes or gate electrode; and (d) measuring an electrical change in the circuit.

Enzyme-based molecular sensors and methods of making and using same are provided. References to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a molecule, composition, process, method, or device that comprises a list of elements does not include only those elements but may include other elements not expressly listed or inherent to such molecules, compositions, processes, methods, or devices.

We claim:

1. A method to obtain a sequence information of a target substrate, the method comprising:
   forming at least one of a voltage or a current circuit, the circuit further comprising:
   a first electrode;
   a second electrode spaced apart from the first electrode;

a first arm molecule having a first end and a second end, the second end of the first arm molecule electrically coupled to the first electrode;

a second arm molecule having a first end and a second end, the second end of the second arm molecule electrically coupled to the second electrode; and a polymerase enzyme, wherein the first end of each of the first and second arm molecules are conjugated to two distinct sites on the polymerase enzyme so that a portion of the polymerase enzyme between the two distinct sites is included in the circuit;

exposing the circuit to a solution having an ionic strength from dissolved ions and the target substrate;

measuring electrical signals through the circuit as the polymerase enzyme engages the target substrate; and processing the electrical signals to identify the sequence information of the target substrate when engaged by the polymerase enzyme;

wherein the target substrate comprises DNA or RNA.

2. The method of claim 1, wherein each of the first and second arm molecules is selected from the group consisting of a double stranded oligonucleotide, a peptide nucleic acid duplex, a peptide nucleic acid-DNA hybrid duplex, a protein alpha-helix, a graphene-like nanoribbon, a natural polymer, a synthetic polymer, and an antibody Fab domain.

3. The method of claim 1, wherein the portion of the polymerase enzyme included in the circuit comprise an internal structural element selected from the group consisting of an alpha-helix, a beta-sheet, and a multiple of such elements in series.

4. The method of claim 1, wherein the two distinct sites on the polymerase enzyme are points on the polymerase enzyme capable of undergoing a conformational change or relative motion during polymerase enzyme function.

5. The method of claim 1, wherein each of the first and second arm molecules comprises a molecule having tension, twist or torsion dependent conductivity.

6. The method of claim 1, wherein the polymerase enzyme comprises an *E. coli* Pol I Klenow Fragment.

7. The method of claim 1, wherein the portion of the polymerase enzyme in the circuit includes an alpha-helix passing through the center of the polymerase enzyme.

8. The method of claim 7, wherein the alpha-helix comprises 37 amino acids.

9. The method of claim 7, wherein the two distinct sites are amino acid positions 508 and 548 in the polymerase enzyme.

10. The method of claim 1, wherein the polymerase enzyme is engineered to have at least one additional charge group.

11. The method of claim 1, wherein the polymerase enzyme comprises a genetically modified form of an *E. coli* Pol I polymerase, a Bst polymerase, a Taq polymerase, a Phi29 polymerase, a T7 polymerase or a reverse transcriptase.

12. The method of claim 1, wherein the two distinct sites in the polymerase enzyme comprise at least one of a native cysteine, a genetically engineered cysteine, a genetically engineered amino acid with a conjugation residue, or a genetically engineered peptide domain comprising a peptide that has a conjugation partner.

13. The circuit of claim 12, wherein the genetically engineered cysteine is present at each of the two distinct sites on the polymerase enzyme.

14. The method of claim 13, wherein the first end of each of the first and second arm molecules comprise a maleimide functionality, and wherein the first end of each of the first and second arm molecules connect to amino acid positions 508 and 548, respectively, by maleimide-cysteine conjugation.

15. The circuit of claim 1, further comprising a third arm molecule connecting the polymerase enzyme to either the first or the second electrode or to a substrate supporting the electrodes.

* * * * *